(12) United States Patent
Thorp et al.

(10) Patent No.: US 7,202,028 B2
(45) Date of Patent: Apr. 10, 2007

(54) METHODS FOR THE ELECTROCHEMICAL DETECTION OF MULTIPLE TARGET COMPOUNDS

(75) Inventors: H. Holden Thorp, Carrboro, NC (US); Ivana V. Yang, Falls Church, VA (US); David H. Stewart, Monrovia, MA (US); John W. Groelke, Raleigh, NC (US); Veronika A. Szalai, Monrovia, MA (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 385 days.

(21) Appl. No.: 10/237,842

(22) Filed: Sep. 9, 2002

(65) Prior Publication Data

US 2003/0152960 A1 Aug. 14, 2003

Related U.S. Application Data

(60) Provisional application No. 60/324,388, filed on Sep. 24, 2001.

(51) Int. Cl.
*C12Q 1/68* (2006.01)
*C12P 19/34* (2006.01)

(52) U.S. Cl. .................. 435/6; 435/91.2; 435/91.5; 435/91.51

(58) Field of Classification Search ............ 435/6, 435/91.2, 91.5, 91.51; 935/77, 78
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,143,854 A | 9/1992 | Pirrung et al. |
| 5,405,783 A | 4/1995 | Pirrung et al. |
| 5,871,918 A | 2/1999 | Thorp et al. |
| 5,968,745 A | 10/1999 | Thorp et al. |
| 6,127,127 A | 10/2000 | Eckhardt et al. |
| 6,132,971 A | 10/2000 | Thorp et al. |
| 2003/0152960 A1 | 8/2003 | Thorp et al. |

FOREIGN PATENT DOCUMENTS

| | | |
|---|---|---|
| EP | 0 478 319 B1 | 4/1997 |
| JP | 3-76600 | 4/1991 |
| WO | WO 85/02627 | 6/1985 |
| WO | WO 91/15768 | 10/1991 |
| WO | WO 93/20230 | 9/1993 |
| WO | WO 94/22889 | 10/1994 |
| WO | WO 95/00530 | 1/1995 |
| WO | WO 97/02359 | 1/1997 |
| WO | WO 98/35232 | 8/1998 |

OTHER PUBLICATIONS

International Search Report of the International Searching Authority for Application No. PCT/US2002/29445 mailed on Jun. 28, 2005.

*Primary Examiner*—Kenneth R. Horlick
*Assistant Examiner*—Joyce Tung
(74) *Attorney, Agent, or Firm*—Myers Bigel Sibley & Sajovec PA

(57) ABSTRACT

A method of detecting two different target molecules through a single electrode is carried out by (a) providing a conductive oxidation-reduction reaction detection electrode; (b) contacting a sample suspected of containing a first and second target molecule to the electrode under conditions in which the first and second target molecules are deposited on the electrode, wherein the first target molecule comprises a first label and the second target molecule comprises a second label; (c) contacting to the electrode a first transition metal complex that oxidizes the first preselected label in a first oxidation-reduction reaction and a second transition metal complex that oxidizes the first and second labels in a second oxidation-reduction reaction, with the first and second oxidation-reduction reactions producing different detectable signals; (d) detecting the presence of the first target molecule by detecting the first oxidation-reduction reaction; and (e) detecting the presence of the second target molecule by detecting the second oxidation-reduction reaction. Devices for carrying out the method are also described.

22 Claims, 11 Drawing Sheets

7-DEAZAADENINE (zA)

7-DEAZAGUANINE (zG)

A.

B.

C.

D.

E.

METHODS FOR THE ELECTROCHEMICAL DETECTION OF MULTIPLE TARGET COMPOUNDS

CROSS REFERENCE TO RELATED APPLICATIONS

This application claims the benefit of U.S. Provisional Application 60/324,388, filed on Sep. 24, 2001, the disclosure of which is incorporated herein by reference in its entirety.

FIELD OF THE INVENTION

The present invention concerns methods for the electrochemical detection of members of specific binding pairs.

BACKGROUND OF THE INVENTION

The detection of individual DNA sequences in heterogenous samples of DNA provides a basis for identifying genes, DNA profiling, and novel approaches to DNA sequencing. One approach to DNA hybridization detection involves the use of surface bound DNA sequences which can be assayed using an analytical response that indicates hybridization of the surface-bound oligomer to a sequence in the heterogeneous sample. These prior analytical methods generally involve laser-induced fluorescence arising from a covalently attached label on the target DNA strand, which methods are not sensitive to single-base mismatches in the surface-bound duplex. For example, U.S. Pat. Nos. 5,143,854 and 5,405,783 to Pirrung et al.; Fodor, et al., Nature 364:555 (1993); Bains, Angew. Chem. 107:356 (1995); and Noble, Analytical Chemistry 67(5):201A (1995) propose surfaces or "chips" for this application. In an alternate method, proposed by Hall, et al., Biochem. and Molec. Bio. Inter. 32(1):21 (1994), DNA hybridization is detected by an electrochemical method including observing the redox behavior of a single stranded DNA as compared to a double stranded DNA. This technique is also not sensitive to single-base mismatches in the DNA sample.

U.S. Pat. Nos. 5,871,918 and 6,132,971 to Thorp et al. describe methods and apparatus for electrically detecting a target molecule by detecting a preselected base in an oxidation-reduction reaction. The methods and apparatus disclosed therein may be used in a variety of applications, including DNA sequencing, diagnostic assays, and quantitative analysis. The methods can advantageously be implemented in a variety of different assay formats and structures, including multi-well plates, with a different assay carried out in each well. However, these references do not describe how to carry out multiple assays in a single well.

SUMMARY OF THE INVENTION

A first aspect of the present invention is a method of detecting two different target molecules through a single common electrode. In general, the method comprises the steps of:

(a) providing a conductive oxidation-reduction reaction detection electrode;

(b) contacting (e.g., by affinity binding, precipitation, etc.) a sample to said electrode, (as discussed further below), said sample suspected of containing a first and second target molecule, under conditions in which the first and second target molecules are deposited on the electrode, wherein the first target molecule comprises a first preselected label, the second target molecule comprises a second preselected label, and the first and second preselected labels are different;

(c) simultaneously contacting to the electrode (i) a first transition metal complex that oxidizes the first preselected label in an oxidation-reduction reaction to cause a first oxidation-reduction reaction between the first transition metal complex and the first preselected label and (ii) a second transition metal complex that oxidizes the first and second preselected labels in an oxidation-reduction reaction to cause a second oxidation-reduction reaction between the second transition metal complex and the second preselected label, from which preselected labels there is electron transfer to the corresponding transition metal complexes resulting in regeneration of the reduced form of the corresponding transition metal complex as part of a catalytic cycle, with the first and second oxidation-reduction reactions producing different detectable signals;

(d) detecting the presence of the first target molecule by detecting the the first oxidation-reduction reaction; and (e) detecting the presence of the second target molecule by detecting the second oxidation-reduction reaction.

The contacting step may be carried out by any suitable means, such as by sandwich assay, competitive assay, direct assay, competitive assay for immobilized target substance, or binding interaction assay, all of which are discussed in greater detail in section H below.

In one embodiment of the foregoing, the sample is suspected of containing a third target molecule; the third target molecule comprises a third preselected label that is different from the first and second preselected labels; the contacting step (c) further comprises contacting to the electrode (iii) a third transition metal complex that oxidizes the first, second and third preselected labels in an oxidation-reduction reaction to cause a third oxidation-reduction reaction between the third transition metal complex and the third preselected label, with the first, second and third oxidation-reduction reactions producing different detectable signals; and the method further comprising the step of: (f) detecting the presence of the third target molecule by detecting the third oxidation-reduction reaction.

In another particular embodiment of the foregoing, the sample is suspected of containing a fourth target molecule; the fourth target molecule comprises a fourth preselected label that is different from the first, second and third preselected labels; the contacting step (c) further comprises contacting to the electrode (iv) a fourth transition metal complex that oxidizes the first, second, third and fourth preselected labels in an oxidation-reduction reaction to cause a fourth oxidation-reduction reaction between the fourth transition metal complex and the fourth preselected label, with the first, second, third and fourth oxidation-reduction reactions producing different detectable signals; the method further comprising the step of: (g) detecting the presence of the fourth target molecule by detecting the fourth oxidation-reduction reaction.

A second aspect of the present invention is a microelectronic device useful for the electrochemical detection of at least two different members of at least two different binding pairs. The device comprises:

(a) a microelectronic substrate;

(b) a conductive oxidation-reduction detection electrode on the substrate;

(c) a first member of a first specific binding pair (for example, a protein, peptide or oligonucleotide probe) immobilized on a non-conductive layer, which first member binds with a second member of the first specific binding pair present in a sample, the first member of the first binding pair being adjacent (or sufficiently close to) the detection electrode so that an oxidation-reduction reaction occurring upon application of a potential to the detection electrode is detectable; and (d) a first member of a second specific binding pair (for example, a protein, peptide or oligonucleotide probe) immobilized on a non-conductive layer that binds with a second member of the second specific binding pair present in a sample, the first member of the second binding pair being adjacent the detection electrode so that an oxidation-reduction reaction occurring upon application of a potential to the detection electrode is detectable; wherein the first member of the first binding pair and the first member of the second binding pair are different.

In one particular embodiment of the foregoing, the device further comprises a first member of a third specific binding pair (for example, a protein, peptide or oligonucleotide probe) immobilized on a non-conductive layer that binds with a second member of the third specific binding pair present in a sample, the first member of the third binding pair being adjacent the detection electrode so that an oxidation-reduction reaction occurring upon application of a potential to the detection electrode is detectable; wherein the first member of the first binding pair, the first member of the second binding pair, and the first member of the third binding pair are different. The device may further include a first member of a fourth binding pair adjacent the detection electrode in like manner as described with the other binding pairs.

In certain embodiments of the foregoing, the microelectronic substrate comprises a sample container, which comprises the conductive oxidation-reduction detection electrode and the immobilized first member of the first and second binding pair.

In certain embodiments, the microelectronic substrate comprises the sample container which comprises a plurality of conductive oxidation-reduction detection electrodes and a plurality of immobilized first members of the first and second binding pairs. In certain embodiments the device further comprises a conductive reference electrode comprising a conducting metal. In certain embodiments the device further comprises a conductive auxiliary electrode comprising a conducting metal. In certain embodiments the oxidation-reduction reaction is detectable via an electrical connection from each conductive oxidation-reduction detection electrode. Thus in certain embodiments the device further comprises an oxidation-reduction reaction detector.

A third aspect of the present invention is a method of detecting at least two different hybridization events through a common electrode, comprising the steps of:

(a) providing a device as described above;

(b) contacting a sample suspected of containing the second member of the first binding pair and the second member of the second binding pair;

(c) simultaneously contacting to the substrate (i) a first transition metal complex that oxidizes the first preselected label in an oxidation-reduction reaction under conditions that cause a first oxidation-reduction reaction between the first transition metal complex and the first preselected label and (ii) a second transition metal complex that oxidizes the first and second preselected labels in an oxidation-reduction reaction under conditions that cause a second oxidation-reduction reaction between the second transition metal catalyst and the second preselected label, from which preselected labels there is electron transfer to the transition metal complex, resulting in regeneration of the reduced form of the corresponding transition metal complex as part of a catalytic cycle, and with the first and second oxidation-reduction reactions producing different detectable signals;

(d) detecting the presence of the second member of the first binding pair from the detection of the first oxidation-reduction reaction; and (e) detecting the presence of the second member of the second binding pair from the detection of the second oxidation-reduction reaction.

Examples of suitable transition metal complexes in the foregoing include, but are not limited to, $Ru(bpy)_3^{2+}$, $Ru(Me_2-bpy)_3^{2+}$, $Ru(Me_2-phen)_3^{2+}$, $Fe(bpy)_3^{2+}$, $Fe(5-Cl-phen)_3^{2+}$, $Os(5-Cl-phen)_3^{2+}$, $Os(bpy)_3^{2+}$, $Os(Me_2-bpy)_3^{2+}$ (full names of which are given below), ferrocene, aminoferrocene, and $ReO_2(py)_4^{1+}$.

In the methods and apparatus herein, examples of suitable preselected labels for nucleic acids include but are not limited to adenine, guanine, and analogs thereof such as, 8-oxoguanine, 8-oxoadenine, 7-deazaguanine, 7-deazaadenine.

In some embodiments of the foregoing, the probe/first member of the first binding pair and probe/first member of the second binding pair are oligonucleotides.

In some embodiments of the foregoing, the probe/first member of the first binding pair and the first member of the second binding pair are peptides or proteins.

In still other embodiments of the foregoing, the probe/first member of the first binding pair is an oligonucleotide; and the probe/first member of the second binding pair is a protein or peptide.

In certain embodiments of the foregoing, the target molecules/second member of the first binding pair and the second member of the second binding pair are proteins or peptides.

In other embodiments of the foregoing, the target molecules/second member of the first binding pair and the second member of the second binding pair are oligonucleotides.

In still other embodiments of the foregoing, the target molecule/second member of the first binding pair is a protein or peptide, and the target molecule/second member of the second binding pair is an oligonucleotide.

In some embodiments of the invention, at least one of the second member of the first binding pair and the second member of the second binding pair is a nucleic acid such as DNA or RNA. Such methods may further comprise the step of amplifying the nucleic acid prior to the contacting step.

In certain embodiments of the foregoing, the electrode is carried by a microelectronic substrate (e.g., silicon or glass).

In certain embodiments of the foregoing, the electrode comprises indium tin oxide.

In certain embodiments of the foregoing, the detecting steps are carried out by multiple step chronoamperometry or cyclic voltametry.

The foregoing and other objects and aspects of the present invention are explained in detail in the specification set forth below.

DETAILED DESCRIPTION OF PREFERRED EMBODIMENTS

Figure 1:
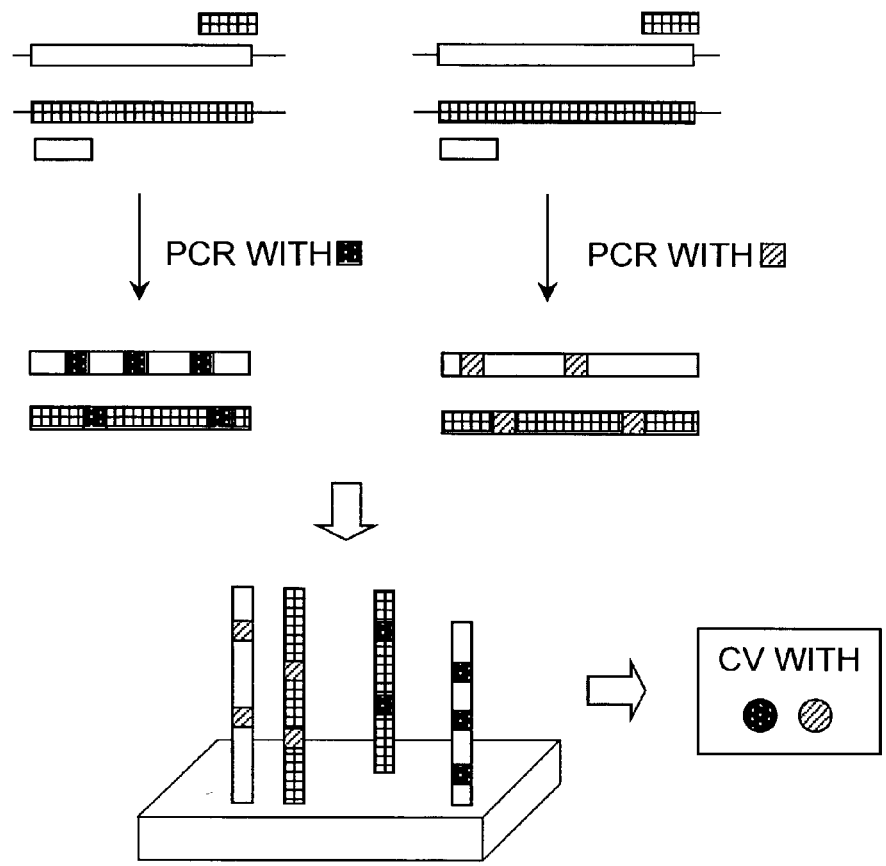
FIG. 1A shows the strategy for simultaneous detection of multiple DNA sequences. Genes of interest are amplified in the presence of modified bases. The resulting PCR products are precipitated onto the ITO surface and detected by voltammetry of metal complexes whose redox potentials match those of the modified bases.
FIG. 1B shows the structures of 7-deazaadenine and 7-deazaguanine.
Figure 1:
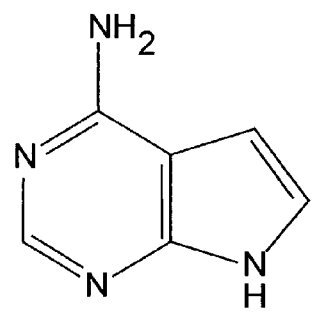
Figure 1:
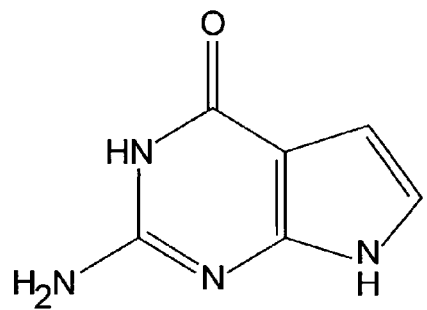

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

"Target molecule" as used herein refers to any type of molecule for which detection may be desired, including but not limited to peptides, proteins, nucleic acids, polysaccharides, lipids, lipoproteins, etc.

"Binding pair" refers to a pair of molecules, one of which may be a target molecule, which members of said pair of molecules specifically and selectively bind to one another. Examples of suitable binding pairs include, but are not limited to: nucleic acid and nucleic acid; protein or peptide and nucleic acid; protein or peptide and protein or peptide; antigens and antibodies; receptors and ligands, haptens, or polysaccharides, etc. Members of binding pairs are sometimes also referred to as "binders" herein.

The term "nucleic acid" as used herein refers to any nucleic acid, including both DNA and RNA. Nucleic acids of the present invention are typically polynucleic acids; that is, polymers of individual nucleotides that are covalently joined by 3', 5' phosphodiester bonds.

The term "complementary nucleic acid" as used herein refers to any nucleic acid, including oligonucleotide probes, that specifically binds to another nucleic acid to form a hybridized nucleic acid.

The phrase "determining the presence or absence of" is intended to include both qualitatively determining and quantitatively determining the presence or absence of the detected event (e.g., DNA hybridization, RNA hybridization, detecting target nucleic acid, etc.).

The terms "hybridized DNA" and "hybridized nucleic acid" refer to a single-stranded DNA which is hybridized to form a double-stranded DNA or nucleic acid, or a double-stranded DNA or nucleic acid which is hybridized to form triple helix DNA or nucleic acid.

The term "probe" as used herein refers to a molecule which specifically binds to another molecule in a binding pair, which probe molecule may be used to determine the presence or absence of the other molecule. Probes may be any member of a binding pair and include, for example, proteins, peptides, natural or synthetic nucleic acids such as DNA or RNA, etc.

The term "sample" as used herein refers to what is applied to or deposited on the electrode, which sample may be derived or obtained from a single source, or derived or obtained from a plurality of sources. The term "deposited on the electrode" as used herein means, for example, that the sample may be deposited (a) on the surface of the electrode, or (b) on the nonconductive layer of the electrode, or (c) on a capture probe on (i) the surface of the electrode, or (ii) on the nonconductive layer, or (iii) adjacent the electrode and sufficiently close thereto so that an oxidation reduction reaction occuring at the probe or at a target captured by that probe is detected at the adjacent electrode.

The phrase "simultaneously contacting" as used herein means that complexes are present on or at a detection electrode at the same time, whether they are added to the electrode simultaneously or sequentially.

While the methods and apparatus of the present invention are sometimes explained with respect to DNA herein, this is for purposes of clarity, and it is to be understood that the methods and apparatus of the instant invention may be applied to other nucleic acids such as RNA, and other targets or members of a specific binding pair such as protein.

The present invention may be carried out utilizing techniques described in, among other things, U.S. Pat. Nos. 5,871,918 and 6,132,971 to Thorp et al., the disclosures of which are to be incorporated by reference herein in their entirety.

A. Labels

In general, a label used to carry out the present invention is any compound, moiety or group that can be oxidized within a suitable voltage range for implementing the present invention, such as a range of about 0 or 0.2 volts up to about 1.4 or 1.6 volts. For example, the labels utilized in the invention may be selected from the group consisting of preselected peptides and preselected nucleotide bases, and may be endogenous or exogenous labels. The labels do not include transition metal complexes, which are used in the invention as mediators to transfer electrons to the conductive substrate. The labels have an oxidation potential approximately equal to or less than that of the transition metal mediator.

When the target molecule is a nucleic acid, the label may be a preselected base on that nucleic acid. Examples of suitable preselected bases include but are not limited to guanine, adenine, 8-oxo-guanine, and 8-oxo-adenine, 8-bromo-guanine, guanosine, xanthosine, wyosine, pseudouridine, 6-mercaptoguanine, 8-mercaptoguanine, 2-thioxanthine, 6-thioxanthine, 6-mercaptopurine, 2-amino-6-carboxymethyl-mercaptopurine, 2-mercaptopurine, 6-methoxypurine, 2-acetylamino-6-hydroxypurine, 6-methylthio-2-hydroxypurine, 2-dimethylamino-6-hydroxypurine, 2-hydroxypurine, 2-aminopurine, 6-amino-2-dimethylallyl-purine, 2-thioadenine, 8-bydroxyadenine, 8-methoxyadenine, 5-aminocytosine, 5-aminouridine, and 6-aminocytosine. Typically, the preselected base is selected from the group consisting of guanine, adenine, 8-oxo-guanine, 8-oxo-adenine, 7-deazaguanine, 7-deazaadenine, 5-aminocytosine, 5-aminouridine, and 6-aminocytosine with guanine being the currently preferred naturally occurring preselected base and 7-deazaguanine the currently preferred synthetic preselected base. Preselected bases that are readily oxidized or reduced can be designed using theoretical methods described in Baik, M.-H. et al., J. Phys. Chem. B (2001), in press.

The method of the invention may be used to electrochemically detect targets containing endogenous labels, for example, particular amino acids in proteins. Endogenous labels are moieties that are contained naturally within any of the binding members of the assay. For the purposes of electrochemical protein detection, endogenous labels are oxidized or reduced in a catalytic reaction with a mediator. In the protein-detection system, these moieties include amino acids that are oxidized by catalytic mediated electrochemistry in the potential range of interest (600–1200 mV) and at potentials below that required for the oxidation of water. This includes cysteine, tyrosine, tryptophan, and histidine. Other amino acids are also oxidizable but not under the assay conditions described here.

Because amino acids oxidizable in the potential range of 600–1200 mV are present in most protein molecules (and hence in target molecules), proteins can be directly detected by catalytic mediated electrochemistry. This is particularly true for large proteins and proteins rich in tryptophan or tyrosine.

Exogenous labels are moieties that are added to binding members or targets by synthetic, artificial, natural, or other means. The role of exogenous labels is to impart electrochemical activity on a molecule that would otherwise be electrochemically inactive or to increase the electrochemical activity of an already active molecule. Examples of exogenous labels used for mediated catalytic electrochemical detection include peptides, peptides with modified amino acids, other proteinaceous electron donor and acceptor compounds, and oligonucleotides containing preselected nucleotide bases that undergo oxidation-reduction by mediated electrochemistry. Other electron donor or acceptor, compounds that can be covalently attached to proteins may be used as labels for electrochemical detection of protein targets and other substances and would be obvious to those skilled in the art. In particular, donor compounds that are oxidized at potentials approximately $\leq 0.6$ V (vs. Ag/AgCl) are useful as labels because they can be oxidized by mediated electrochemistry under conditions in which there is no background signal from oxidation of nucleic acids or amino acids present in the assay. Examples of low-potential labels are peptides containing the modified amino acids 5-hydroxytryptophan; 3-aminotyrosine; and 3,4-dihydroxyphenylalanine. These modified amino acids each have an oxidation potential approximately $\leq 0.47$ V (vs. Ag/AgCl) and are well-suited to react in a mediated catalytic oxidation-reduction reaction with the transition metal mediator, $Os(Me_2\text{-}bpy)_3^{2+}$, which has an oxidation-reduction potential of about 0.47 V (vs. Ag/AgCl).

A number of labels that have been previously described for detection of binding interactions are not well-suited for use herein and are not included in this application. For example, omitted as labels for mediated electrochemical detection are transition metal complexes and enzyme labels that require a substrate to generate electrochemical or optical signal through enzymatic catalysis. In the mediated catalytic electrochemical detection of the invention, the transition metal complex acts as a catalyst and not as a label.

B. Transition Metal Complex Mediators of Oxidation-Reduction Reactions

A mediator used to carry out the present invention is any compound, typically a transition metal complex, that enables or makes possible electron transfer to a corresponding label as described above. In general, a different mediator will be used for each label, to which a particular mediator corresponds. The mediator may be any molecule such as a cationic, anionic, non-ionic, or zwitterionic molecule that is reactive with the electrochemical label at a unique oxidation potential to transfer electrons from the label to the electrode. It is important that the mediators used in the invention herein be selected to exhibit a reversible redox couple at about the same oxidation potential or higher than that observed for the label that is being detected. Thus, to use tyrosine or tryptophan as the label, the mediator must have an oxidation potential of about $\geq 0.65$ V or $\geq 0.8$ V vs. Ag/AgCl, respectively. Suitable mediators would be $Os(bpy)_3^{2+}$ and $Fe(bpy)_3^{2+}$, respectively. Similarly, in order to use guanine as the label, the mediator must have an oxidation potential about $\geq 1.1$ V vs. Ag/AgCl, and an appropriate mediator is $Ru(bpy)_3^{2+}$. Other examples of suitable mediators for use in the methods of the present invention are transition metal complexes, including, for example, Ruthenium 2+(2,2'-bipyridine)$_3$ ("$Ru(bpy)_3^{2+}$"); Ruthenium2+(4,4'-dimethyl-2,2'-bipyridine)$_3$ ("$Ru(Me_2-bpy)_3^{2+}$"); Ruthenium2+(5,6-dimethyl-1,10-phenanthroline)$_3$ ("$Ru(Me_2-phen)_3^{2+}$"); Iron2+(2,2'-bipyridine)$_3$ ("$Fe(bpy)_3^{2+}$"); Iron2+(4,4'-dimethyl-2,2'-bipyridine)$_3$ ("$Fe(Me_2-bpy)_3^{2+}$"); Iron2+(5-chlorophenanthroline)$_3$ ("$Fe(5-Cl-phen)_3^{2+}$"); Iron2+(4,4'-dimethyl-2,2'-bipyridine)(bipyridine)$_2$ ("$Fe(Me_2-bpy)(bpy)_2^{2+}$"); $Iron^{2+}$(4,4'-dimethyl-2,2'-bipyridine)$_2$(bipyridine) ("$Fe(Me_2-bpy)_2(bpy)^{2+}$"); Osmium2+(2,2'-bipyridine)$_3$ ("$Os(bpy)_3^{2+}$"); $Osmium^{2+}$(4,4'-dimethyl-2,2'-bipyridine)$_3$ ("$Os(Me_2-bpy)_3^{2+}$"); $Osmium^{2+}$(5-chlorophenanthroline)$_3$ ("$Os(5-Cl-phen)_3^{2+}$"); Osmium2+(4,4'-dimethyl-2,2'-bipyridine)(bipyridine)$_2$ ("$Os(Me_2-bpy)(bpy)_2^{2+}$"); $Osmium^{2+}$(4,4'-dimethyl-2,2'-bipyridine)$_2$(bipyridine) ("$Os(Me_2-bpy)_2(bpy)^{2+}$"); dioxorhenium$^{1+}$phosphine; and dioxorhenium$^{1+}$pyridine ("$ReO_2(Py)_4^{1+}$"). Some anionic complexes useful as mediators are: $Ru(bpy)((SO_3)_2-bpy)_2^{2-}$ and $Ru(bpy)((CO_2)_2-bpy)_2^{2-}$ and some zwitterionic complexes useful as mediators are $Ru(bpy)_2((SO_3)_2-bpy)$ and $Ru(bpy)_2((CO_2)_2-bpy)$ where $(SO_3)_2-bpy^{2-}$ is 4,4'-disulfonato-2,2'-bipyridine and $(CO_2)_2-bpy^{2-}$ is 4,4'-dicarboxy-2,2'-bipyridine. Derivatives of the ferrocene molecular are also excellent mediators. Suitable substituted derivatives of the pyridine, bipyridine and phenanthroline groups may also be employed in complexes with any of the foregoing metals. Suitable substituted derivatives include but are not limited to 4-aminopyridine; 4-dimethylpyridine; 4-acetylpyridine; 4-nitropyridine; 4,4'-diamino-2,2'-bipyridine; 5,5'-diamino-2,2'-bipyridine; 6,6'-diamino-2,2'-bipyridine; 5,5'-dimethyl-2,2'-bipyridine; 6,6'-dimethyl-2,2'-bipyridine; 4,4'-diethylenediamine-2,2'-bipyridine; 5,5'-diethylenediamine-2,2'-bipyridine; 6,6'-diethylenediamine-2,2'-bipyridine; 4,4'-dihydroxyl-2,2'-bipyridine; 5,5'-dihydroxyl-2,2'-bipyridine; 6,6'-dihydroxyl-2,2'-bipyridine; 4,4',4"-triamino-2,2',2"-terpyridine; 4,4',4"-triethylenediamine-2,2',2"-terpyridine; 4,4',4"-trihydroxy-2,2',2"-terpyridine; 4,4',4"-trinitro-2,2',2"-terpyridine; 4,4',4"-triphenyl-2,2',2"-terpyridine; 4,7-diamino-1,10-phenanthroline; 3,8-diamino-1,10-phenanthroline; 4,7-diethylenediamine-1,10-phenanthroline; 3,8-diethylenediamine-1,10-phenanthroline; 4,7-dihydroxyl-1,10-phenanthroline; 3,8-dihydroxyl-1,10-phenanthroline; 4,7-dinitro-1,10-phenanthroline; 3,8-dinitro-1,10-phenanthroline; 4,7-diphenyl-1,10-phenanthroline; 3,8-diphenyl-1,10-phenanthroline; 4,7-disperamine-1,10-phenanthroline; 3,8-disperamine-1,10-phenanthroline; dipyrido[3,2-a:2',2'-c]phenazine; 4,4'-dichloro-2,2'-bipyridine; 5,5'-dichloro-2,2'-bipyridine; and 6,6'-dichloro-2,2'-bipyridine.

C. Oxidation-Reduction Reaction

The mediator may be reacted with labels in or on the captured target, the surrogate target, or the binder under conditions sufficient to effect the oxidation-reduction reaction of the mediator with the label via a catalytic reaction. The solution in which the oxidation-reduction reaction takes place may be any suitable solution for solubilizing the components of the assay and preferably comprises water. Suitable conditions for permitting the oxidation-reduction reaction to occur will be known to those skilled in the art.

D. Detection of Oxidation-Reduction Reactions

The occurrence of the oxidation-reduction reaction of the invention may be detected according to any suitable means known to those skilled in the art. For example, the occurrence of the oxidation-reduction reaction may be detected using a detection (working) electrode to observe a change in the electrochemical signal, which is indicative of the occurrence of the oxidation-reduction reaction. An electrode suitable for the detection of labels in accordance with the methods described herein comprises a conductive substrate having a working surface thereon, and is sensitive to the transfer of electrons between the mediator and the label. The conductive substrate may be a metallic substrate or a non-metallic substrate, including semiconductor substrates. Preferably the electrode is a tin-doped indium oxide (ITO) electrode, a tin-oxide or an indium oxide electrode. Alternatively, the electrode may be of gold, carbon fiber, carbon paste, or glassy carbon. The suitability of a particular electrode material ultimately is dependent on the utility of that material with the selected label(s) and mediator(s) at their required redox potentials. The conductive substrate may take any physical form, such as an elongate shaped device having a working surface formed on one end thereof, or a flat sheet having the working surface on one side thereof, for example in the wells of a microtiter plate.

In order to prepare the electrode for modification with immobilized biological binding entities, the electrode is modified with a suitable nonconductive layer. The nonconductive layer may have one or more of a number of functions including providing covalent attachment of biomolecules, blocking of nonspecific binding to the electrode, and allowing electron transfer between the mediator and the electrode and/or the mediator and the label. The nonconductive layer may be one or more of the following, for example: self-assembled monolayers (e.g., U.S. Pat. No. 6,127,127); cross-linked polymer layers; alkyl silane layers; alkylphosphonate-, alkylphosphate-, carboxyalkane-, alkanethiol-, or alkylamine-based layers; polymer membranes (as in U.S. Pat. No. 5,968,745) and/or one or more layers of biomolecules such as proteins, antibodies, biotin-binding molecules (avidin, streptavidin, neutravidin), protein A, protein G, receptors, or oligonucleotides. In the case of a nonconductive layer comprised of biomolecules, the nonconductive layer can serve as a capture layer for the binder, target protein, the surrogate target, or the affinity ligand. For example, on an electrode designed to detect human chorionic gonadotropin (hCG), the nonconductive layer could be an anti-hCG capture antibody; on an electrode designed to detect a ligand, a receptor molecule could serve as the nonconductive layer. Alternatively, the nonconductive layer can be a biomolecule that binds the capture molecule such as protein A for a capture antibody or an antibody directed against the capture molecule (i.e. an anti-streptavidin antibody for a binding assay using streptavidin as the capture molecule or an anti-receptor antibody for a receptor-based assay). Regardless of the nature of the nonconductive layer, this layer will ultimately be placed in contact with a solution containing the mediator prior to electrochemical detection.

Generally, a reference electrode and an auxiliary electrode are also placed in contact with the mediator solution in conjunction with the detection electrode. Suitable reference electrodes are known in the art and include, for example, silver/silver chloride (Ag/AgCl) electrodes, saturated calomel electrodes (SCE), and silver pseudo reference electrodes. A suitable auxiliary electrode is a platinum electrode.

The detection of the electrochemical signal produced by the catalytic oxidation-reduction of labels permits the determination of the presence or absence of specific substances in a sample. As used herein, terms such as determining or detecting "the presence or absence" of a substance as used to describe the instant invention, also include quantitation of the amount of the substance. In the invention, the transition metal mediator is oxidized by an electrode. Then, the mediator is reduced by the label and then reoxidized at the electrode. Thus, there is electron transfer from the label to the transition metal mediator resulting in regeneration of the reduced form of the transition metal mediator as part of a catalytic cycle. The step of determining the presence or absence of target in a sample typically includes: (i) measuring the electrochemical signal generated by the oxidation-reduction reaction of the mediator at electrodes that are and are not capable of specifically binding the target, (ii) comparing the measured signal from the transition metal complex at both electrodes, and then (iii) determining whether or not the electrochemical signal generated from the mediator at the electrode that is capable of binding the target is essentially the same as, greater than, or less than, the electrochemical signal generated from the mediator at the electrode that does not bind the target. The step of measuring the electrochemical signal may be carried out by any suitable means. For example, the difference in electrochemical signal may be determined by comparing the electrochemical signal (such as current or charge) from electrodes which are and are not capable of binding the target at the same scan rate, mediator concentration, buffer condition, temperature, and/or electrochemical method.

The electrochemical signal associated with the oxidation-reduction reaction may be measured by providing a suitable apparatus in electronic communication with the detection electrode. A suitable apparatus is a potentiostat capable of measuring the electronic signal that is generated so as to provide an indication of whether or not a reaction has occurred between the label and the mediator. The electronic signal may be characteristic of any electrochemical method, including cyclic voltammetry, normal pulse voltammetry, chronoamperometry, and square-wave voltammetry, with chronoamperometry and cyclic voltammetry being the currently preferred forms.

In cyclic voltammetry, the potential of the electrochemical system is varied linearly from an initial potential between 0–800 mV to a final potential between 500–1600 mV at a constant scan rate (0.01 mV/s to 200 V/s). When the final potential is reached, the scan direction is reversed and the same potential range is swept again in the opposite direction. The preferred scan rate for $Ru(bpy)_3^{2+}$ is 1–20 V/s with a 0 mV initial potential and a 1400 mV final potential. The current is collected at each potential and the data is plotted as a current versus potential scan. For lower-potential mediators, such as $Os(bpy)_3^{2+}$ and $Os(Me_2\text{-}bpy)_3^{2+}$, instead of scanning from between 0–800 mV to between 500–1600 mV, it is preferable to scan from about between 0–100 mV to between 300–1000 mV (vs. a Ag/AgCl reference electrode) because of the lower redox potentials required to oxidize these mediators.

In chronoamperometry as used in the invention herein, the electrochemical system is stepped from an initial potential between 0 mV–800 mV directly to a final potential between 500–1600 mV and held there for some specified period of time (50 µs to 10 s) and the current is collected as a function of time. If desired, the potential can be stepped back to the initial potential, and the current can be collected at the initial potential as a function of time. The preferred potential step for $Ru(bpy)_3^{2+}$ is from between 0–800 mV to 1300 mV (vs. Ag/AgCl) with a collection time of from 50–1000 ms. For lower potential mediators, such as $Os(bpy)_3^{2+}$ and $Os(Me_2\text{-}bpy)_3^{2+}$, it is preferable to step from about 0–100 mV to 300–1000 mV (vs. Ag/AgCl).

In chronocoulometry, a potential step is also applied. For use in the invention herein, starting at the initial potential (0 mV–800 mV), the electrochemical system is stepped directly to the final potential (500 mV–1600 mV). The electrochemical system is held at the final potential for some specified period of time (50 µs to 10 s) and the charge is collected as a function of time. Although not presently done, if desired, the potential can be stepped back to the initial potential and the charge can be collected at the initial potential as a function of time.

The typical apparatus that would be used for the invention herein, may, for example, include a sample container for holding a fluid sample; an electrode, as described above; and a potentiostat in electronic communication with the electrode surface. In addition, the apparatus preferably comprises a first member of a binding pair, such as a capture antibody, attached to the electrode or to a nonconductive layer on the electrode surface. The invention may be used with a microelectronic device comprising a microelectronic substrate having first and second opposing faces, a conductive electrode on the first face, and an immobilized binder for the target substance on the second face sufficiently close to the first face to permit detection of an oxidation-reduction reaction on the second face. The oxidation-reduction reaction assay format may be in either: 1) a sandwich format wherein a target substance, captured by the immobilized first binder, is detected by a second labeled binder for the target substance, 2) a direct format wherein the target substance is captured by the immobilized first binder and is detected directly through labels bound to the target, 3) a competitive format using a labeled target or labeled surrogate target which competes with the target substance in the sample for binding to the immobilized binder, 4) a competitive format using a labeled binder and immobilized target substance with which the target substance in the sample competes for binding of the labeled binder, or 5) a binding assay format using an immobilized first binder, a second labeled binder, and a test sample which may or may not affect the interaction between the two binders.

E. Deconvolution of Signals

When a cyclic voltammogram of two mediators is obtained, two peak currents can be measured at the potentials that correspond to each mediator. If the sample is suspected of containing one or both of two particular DNA sequences, then a preselected base is chosen for each sequence. The first preselected base will be oxidized at a higher potential than the second preselected base. For example, the first preselected base may be 7-deazaadenine. This base is oxidized by $Ru(bpy)_3^{2+}$, so the first mediator is $Ru(bpy)_3^{2+}$. The second preselected base is then chosen to have a lower potential than the first preselected base. A second mediator is then chosen to have a lower potential than the first mediator, but one that is high enough to oxidize the second preselected base. For example, the second preselected base in this case may, for example, be 7-deazaguanine. A second mediator that oxidizes 7-deazaguanine but not 7-deazaadenine would be $Ru(Me_2bpy)_3^{2+}$. Because the potential of the second preselected base is lower than that of the first preselected base, the second preselected base will also be oxidized by the first mediator. Thus, the current from the first mediator will be increased by the presence of either the first or second preselected base, while the current of the second mediator will be increased by the presence of only the second preselected base. In the simplest analysis, if there is current enhancement for the second mediator, that is used to determine the quantity of the second preselected base. This quantity is then subtracted from the current enhancement observed at the first mediator. The remaining current enhancement for the first mediator can be attributed to the presence of the first preselected base.

In practice, the contribution of the second preselected base to the current for the first mediator may be lower than the contribution of the second preselected base to the current for the second mediator. This will occur because if the second mediator is oxidized before the first mediator in a voltammetric sweep, some of the second preseleced base will be oxidized before the first mediator is oxidized, leaving less of the second preselected base to be oxidized by the first mediator. This effect can be determined in standard calibration curves and used to assign current enhancements from the first mediator to appropriate combinations of base concentrations.

Deconvolution with signals from additional preselected bases or labels (e.g., third, fourth) may be carried out in like manner as described above.

F. Quantitating Target Binding

The herein-described method is particularly well-suited to the quantitative detection of nucleic acid and protein targets and other binding substances. In the case described in this section, the rate constant for oxidation of labels associated with the bound target by the mediator can be determined from the cyclic voltammogram by digital simulation. Under most conditions, this reaction will obey second-order kinetics, so the rate=k[mediator][label] where k is the rate constant that is specific for the particular label, [mediator] is the concentration of the mediator, and [label] is the concentration of label. If k and [mediator] are known, then the quantity of the label, and thus of the target, can be determined. In practice, a calibration curve for the current enhancements obtained with different quantities of standard solutions containing label is constructed so that the electrochemical signal enhancement observed for an electrode treated with a test sample can be used to obtain directly the quantity of label (and target) bound to the electrode. This quantity is then related directly to the quantity of target present in the test sample.

G. Nucleic Acid Amplification Methods

Inasmuch as the processes of the present invention involve contacting the DNA sample to an oligonucleotide probe to produce a hybridized DNA, it may be desirable for certain applications to amplify the DNA prior to contacting with the probe. In addition, the amplification process can be used to introduce synthetic preselected bases into the target, either by including one or more preselected bases in the primer(s) used in the amplification process or by using a triphosphate of the preselected base in the amplification mixture, i.e., by substituting 7-deazaguanosine-5'-triphosphate for guanosine-5'-triphosphate in the amplification reaction.

Amplification of a selected, or target, nucleic acid sequence may be carried out by any suitable means. See generally D. Kwoh and T. Kwoh, Am. Biotechnol. Lab. 8, 14–25 (1990). Examples of suitable amplification techniques include, but are not limited to, polymerase chain reaction (including, for RNA amplification, reverse-transcriptase polymerase chain reaction), ligase chain reaction, strand displacement amplification, transcription-based amplification (see D. Kwoh et al., Proc. Natl. Acad. Sci. USA 86, 1173–1177 (1989)), self-sustained sequence replication (or "3SR") (see J. Guatelli et al., Proc. Natl. Acad. Sci. USA 87, 1874–1878 (1990)), the Q.beta. replicase system (see P. Lizardi et al., Biotechnology 6, 1197–1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra). The bases incorporated into the amplification product may be natural or modified bases (modified before or after amplification), and the bases may be selected to optimize subsequent electrochemical detection steps. Techniques for amplification are known and described in, among other things, U.S. Pat. Nos. 4,683,195; 4,683,202; 4,800,159; and 4,965,188; G. Walker et al., Proc. Natl. Acad. Sci. USA 89, 392–396 (1992); G. Walker et al., Nucleic Acids Res. 20, 1691–1696 (1992); R. Weiss, Science 254, 1292 (1991).

H. Assay Formats

The general methods of contacting a sample and then detecting of binding interaction in instant invention can be carried out in any suitable assay format, including but not limited to conventional sandwich assays, competitive assays, or assays with direct target detection. These assays may be based on immunological affinity or on affinities that are based on receptor-ligand, protein-protein, nucleic acid-nucleic acid, or nucleic acid-protein interactions. Cell receptors for proteins which can be used in the instant invention as binders include but are not limited to receptors for transport proteins (i.e., transferrin receptor) (Testa, U., et al., Crit. Rev. Oncog., 1993, 4, 241), receptors for hormone/growth factors (i.e., epidermal growth factor, insulin, nerve growth factor) (Ullrich, A. et al., Cell, 1990, 61 203; Baxter, R. C., Am. J. Physiol. Endocrinol. Metabol., 2000, 278, E967), and G-protein coupled receptors for hormones such as luteinizing hormone, follicle-stimulating hormone, and thyroid stimulating hormone (Schoneberg, T., et al., Mol. Cell Endocrinolo., 1999, 151 181). Receptors of bacterial origin (Modun, B. J., et al., Microbiology, 1998, 144 1005; Schryvers, A. B., et al., Adv. Exp. Med. Biol., 1998, 443 123) and viral origin (Bella, J., et al., J. Struct. Biol, 1999, 128 69;

Domingo, E., et al., *Virus Res.,* 1999, 62 169) may also be used in the instant invention. Extracellular matrix proteins (ECM) can be used to detect ECM-binding proteins (Najjam, S., et al., *Cytokine,* 1997, 9 1013). DNA can be immobilized as a binding member for DNA-binding proteins such as transcription factors (activators, repressors, or regulators) (McGown, L. B., et al., *Anal. Chem.,* 1995, 67 663A). Mediated electrochemical detection of binding interactions may also be utilized to evaluate drug candidates for their effects on protein-protein and other biological interactions. As such, the technology described here provides a versatile binding assay for drug discovery which can be applied to a variety of drug target-drug interactions. As used herein the term "target protein" includes proteins, glycoproteins, lipoproteins, protein fragments, polypeptides, glycoprotein fragments and lipoprotein fragments.

1. Sandwich. Briefly, in the sandwich assay format, the procedure consists of modifying the electrode with the first member of the binding pair (i.e., antibody, receptor, or DNA), adding the sample, which may or may not contain the target protein or target substance, then adding the second binding member, washing to remove unbound reagents, and adding mediator. Electrochemical interrogation is performed, and enhanced cyclic voltammetry or chronoamperometry signal relative to a control indicates the presence of the target protein or target substance in the sample.

In this format, the target in the sample is detected via capture by a solid-phase immobilized first binder, such as an antibody, antibody fragment, receptor protein or DNA to form a target complex, followed by the binding of the captured target by a labeled second binder to form a 3-member target complex. In a preferred embodiment, the second binder contains only endogenous labels (i.e., electrochemically active amino acids) and the presence of target in a sample is evident from the increased current generated by the target complex. In contrast, significantly less current is generated with samples not containing the target since complex formation does not occur, and thus, current is generated only by any endogenous label in the solid phase immobilized binder alone.

In a second preferred embodiment of the sandwich assay, the current generated by the first preferred embodiment is enhanced by the addition of a third binder that recognizes the second binder on the target complex to create a 4-member complex. This is analogous to the use of secondary binders in classical immunoassays. The preferred mediator for the first two embodiments (above) is $Ru(bpy)_3^{2+}$ which has a potential of about 1.05 V or $Os(bpy)_3^{2+}$ which has a potential of 0.65 V (vs. Ag/AgCl).

In a third preferred embodiment of the sandwich assay format, the second or third binder is covalently labeled with labels such as oligonucleotides, proteins, peptides, or peptides containing modified amino acids with lower redox potentials (approximately $\leq 0.6$ V vs. Ag/AgCl). Mediators matched to these lower potentials, such as $Os(Me_2\text{-}bpy)_3^{2+}$, are used with the low potential labels. In addition, the second or third binder may be labeled with certain electron donor compounds that also have low potentials. The second and third binders for each analyte can be chosen with a preselected base corresponding to a particular analyte such that multiple assays can be conducted where in each assay, a different preselected base is chosen for each second or third binder.

In the instant invention, an alternative to the above sequence steps for the method of detection is to mix the sample with the second binder prior to exposure of the mixture to the immobilized first binder, such that the binding of the second binder occurs prior to binding of the target to the immobilized first binder.

2. Competitive. In the competitive assay format, the target competes with a labeled target for binding to an immobilized binder. For example, the beta chain of the hormone, human chorionic gonadotropin (hCG), can be labeled with a peptide rich in tyrosine or an oligonucleotide containing guanine and shown to bind to rabbit antibody specific for the beta chain of hCG. The detection of hCG in a sample is possible by the competition of the hCG with the labeled beta chain for the beta chain-specific antibody. In this scenario, the electrochemical signal is high in the absence of target hCG, and the electrochemical signal decreases if target hCG competes with the labeled beta-chain for the immobilized hCG beta chain-specific antibody. In a similar manner, a labeled surrogate target bound to an immobilized binder may be displaced by target present in a test sample, resulting in a decrease in electrochemical signal. The competitive format is particularly suitable for detecting binding interactions of small molecules such as drugs, steroids and vitamins.

3. Direct. In the direct target detection assay, the steps are the same as for the sandwich assay except a labeled second binder is not added. The labeled second binder is not required in this case because the target protein has the property of being electrochemically active itself, and allows direct mediated electrochemical detection of the target. This approach can be used particularly for large proteins (i.e., $\geq 150$ kD), such as antibodies or other globulins that contain many amino acids and thus are able to generate a significant electrochemical current by themselves through a catalytic oxidation-reduction reaction with a mediator such as $Ru(bpy)_3^{+2}$.

4. Competitive Assay for Immobilized Target Substance. In this format, a target substance or surrogate target substance is immobilized on the electrode surface and exposed to the sample (which may or may not contain the target substance) and a labeled binder (either endogenous or exogenous). As is normally used in this art, for example, in drug discovery, the surrogate target substance has a lower binding affinity than the target substance for the labeled binder. In this embodiment of the invention, the electrochemical signal is high in the absence of the target substance in the sample due to the binding of the labeled binder to the immobilized surrogate target substance, and the electrochemical signal decreases if target substance present in the sample competes with the immobilized surrogate target substance for binding of the labeled binder.

5. Binding Interaction Assay. In this format, a first binder that is a member of a binding pair is immobilized on the electrode surface. The immobilized binder is exposed to a test sample and to a second binder that is a member of the binding pair in order to determine the effect of the test sample on the binding interaction between the first and second binders. The test sample may comprise a substance that facilitates, inhibits, or does not affect binding of the two binders. For example, the test sample could contain a drug candidate that prevents two proteins from binding to each other, or the test sample could contain a drug candidate that enhances the binding interaction. Thus, this assay format can be used to screen potential drug compounds in order to determine the effect they have on a binding interaction. The mode of action by which the test sample affects the binding interaction includes but is not limited to blocking or enhancing the binding of one of the binders and inducing a conformational change in the binding site. In contrast to the above assay formats where the intention is to detect the presence or absence of a substance using catalytic mediated electrochemistry, the binding interaction assay format is designed to detect the effect of a substance on a binding interaction between members of a binding pair using catalytic mediated electrochemistry.

I. Electrode Structures and Devices

An electrode useful for the electrochemical detection of a preselected base in a nucleic acid in accordance with the methods described above comprises: (a) a conductive substrate having a working surface formed thereon; and (b) a nonconductive (e.g. polymer) layer connected to the working surface. The polymer layer is one that binds the members of the first, second, third, or fourth (etc.) binding pairs (e.g., by hydrophobic interaction or any other suitable binding technique) and is porous to the transition metal complex (i.e., the transition metal complex can migrate to the nucleic acid bound to the polymer). The members of the binding pairs (e.g., probes or "binders") may be immobilized on the nonconductive layer in accordance with known techniques. The conductive substrate may be a metallic substrate or a non-metallic substrate, including semiconductor substrates (e.g., gold, glassy carbon, indium-doped tin oxide, etc.). The conductive substrate may take any physical form, such as an elongate probe having a working surface formed on one end thereof, or a flat sheet having the working surface formed on one side thereof. The nonconductive layer may be connected to the working surface by any suitable means, such as by clamping the polymer layer to the working surface, evaporation of a solution of the polymer onto the electrode, or electropolymerization. Exemplary nonconductive materials include polymers such as nylon, nitrocellulose, polystyrene, poly(vinylpyridine), silanes or polysilanes, etc., and other materials such as streptavidin, avidin, protein A, protein G, and antibodies. The thickness of the nonconductive layer is not critical, but can be from 100 Angstroms to 1, 10, or even 100 microns. The electrode may be used in essentially all of the methods described above.

An advantage of the techniques described above is that they may be carried out with a microelectronic device. A microelectronic device useful for the electrochemical detection of a nucleic acid species in the methods described above comprises a microelectronic substrate having first and second opposing faces; a conductive electrode on the first face (with or without a nonconductive layer connected thereto as described above); and an oligonucleotide capture probe immobilized on the first face adjacent the conductive electrode, or alternatively on the nonconductive layer on the electrode. The capture probe may, in addition, be spaced sufficiently close to the adjacent electrode (e.g., from about 0.1, 1, or 2.mu. up to about 50, 100, 500 or even 1000.mu.) so that an oxidation reduction reaction occuring at that probe, or at a target nucleic acid hybridized to that probe, is detected at the adjacent electrode.

In the preferred embodiment, a microelectronic device has a plurality of separate electrodes on the first opposing face, and a plurality of separate capture probes immobilized adjacent to each of the separate electrodes. By providing a plurality of separate probes, differing from one another, each with an associated electrode, a single, compact device is provided that can detect a variety of different hybridization events. Each electrode is electrically connected to a suitable contact so that the device may be wired or otherwise operatively associated with the necessary electronic equipment for carrying out the detection and determining steps of the methods described herein.

The probe may be selectively immobilized at the appropriate location on the microelectronic substrate by known techniques. See, e.g., U.S. Pat. No. 5,405,783 to Pirrung et al. The microelectronic substrate may be a semiconductor (e.g., silicon) or non-semiconductor materials that can be processed using conventional microelectronic techniques (e.g., glass). The electrode may be metal or a non-metallic conductive material, such as polycrystalline silicon. The electrode can be formed using conventional microelectronic processing techniques, such as deposition etching. A variety of suitable microelectronic structures and fabrication techniques are well known to those skilled in the art. See, e.g., S. M. Sze, VLSI Technology (1983); S. K. Ghandhi, VLSI Fabrication Principles (1983).

The examples, which follow, are set forth to illustrate the present invention, and are not to be construed as limiting thereof. In the following examples, bp means base pair, cDNA means copy DNA, μg means microgram, ORF means open reading frame, and min means minute.

EXAMPLE 1

Materials and Methods

Materials. Synthetic oligonucleotide primers were purchased from the Nucleic Acid Core Facility at the Lineberger Comprehensive Cancer Center at the University of North Carolina at Chapel Hill with no additional purification. Water was purified with a MilliQ purification system (Millipore). Reagents for buffer preparation were purchased from Gibco BRL or Mallinckrodt. SeaKem LE agarose was purchased from FMC BioProducts. [Ru(bpy)$_3$]Cl$_2$ was purchased from Aldrich and purified by recrystallization from methanol. [Ru(Me$_2$bpy)$_3$]Cl$_2$ (Me$_2$bpy=4,4'-dimethyl-2,2'-bipyridyne) and [Fe(bpy)$_3$]Cl$_2$ were prepared as previously described (DeSimone and Drago (1970) *J. Am. Chem. Soc.* 92:2343–2352; Mabrouk and Wrighton (1986) *Inorg. Chem.* 25:526–531). Unmodified dNTPs were purchased from Pharmacia, and 7-deaza analogs were obtained from Roche.

Instrumentation. All solution concentrations were determined spectrophotometrically using a Hewlett-Packard HP 8452 diode array spectrophotometer. The extinction coefficients used were $\epsilon_{452}$=14 600 M$^{-1}$cm$^{-1}$ for Ru(bpy)$_3^{2+}$, $\epsilon_{524}$=8 400 M$^{-1}$cm$^{-1}$ for Fe(bpy)$_3^{2+}$, $\epsilon_{458}$=17 000 M$^{-1}$cm$^{-1}$ for Ru(Me$_2$bpy)$_3^{2+}$(Ford-Smith and Sutin (1961) *J. Am. Chem. Soc.* 83:1830–1834; Mabrouk and Wrighton (1986) *Inorg. Chem.* 25:526–531). Extinction coefficients for oligonucleotides were calculated using the nearest neighbor equation, giving the concentration of nucleic acid in strand concentration (Fasman (1976) CRC Handbook of Biochemistry and Molecular Biology, Section B (Cleveland, Ohio: CRC Press)).

Polymerase Chain Reaction. Each 100-μL reaction contained 1.2 ng of template, 200 μM each dATP/7-deaza-dATP, dCTP, dGTP/7-deaza-dGTP, and dTTP, 400 nM each of the primers (up and down, or up and mid; see FIG. 6.2 for primer sequences), 2 mM MgCl$_2$, 5 U Taq polymerase (Gibco BRL), and 1× buffer provided with the Taq polymerase. Amplification was performed on a PCRSprint thermocycler (Hybaid) with an initial denaturation step at 94° C. for 3 min, followed by 40 cycles with the following profile: denaturation for 1 min at 94° C., annealing for 1 min at 63° C., and extension for 45–60 sec at 72° C. A final extension step at 72° C. for 5 min was included at the end of the amplification. PCR products were purified using the QIAquick PCR purification kit (Qiagen) according to manufacturer's instructions.

Restriction Digest. Each restriction enzyme digest contained 3–8 μL of the purified PCR product and 1×NEB buffer 4. Reactions were incubated for 1 h at 25° C. in the presence of 10 U SmaI or at 37° C. in the presence of 2.5 U ClaI or NspI. The resulting fragments were separated by size on a 2% agarose gel at 100 V for 1–2 h. The gel was stained with ethidium bromide (Sigma) and visualized using a CCD camera (Spectroline). The sizes of DNA fragments were estimated by comparison to the ϕX174/HaeIII DNA ladder (Gibco BRL).

DNA Immobilization. ITO electrodes were cleaned by 15-minute sonications in 2-propanol, and MilliQ water twice. A solution containing 3 μL of the desired concentration of the PCR product in 100 mM NaOAc/HOAc, pH 6.8 was added to 27 μL dimethylformamide (DMF). The resulting solution was transferred to the center of the electrode and incubated in a constant humidity chamber for 1 h. Electrodes were then washed with MilliQ water twice, 1 M NaCl once, and MilliQ water three times (3 minutes each wash), and air-dried.

Phosphorimagery. ITO electrodes for phosphorimagery were prepared in the same fashion as for voltammetry experiments, except that a portion of the DNA solution was 5'-[$^{32}$P]-labeled using T4 polynucleotide kinase (Gibco BRL) and 5'-[γ-$^{32}$P]-dATP (Amersham) (Sambrook et al. (1989) Molecular Cloning: a Laboratory Manual (Plainview, N.Y.: Cold Spring Harbor)). Unreacted 5'-[γ-$^{32}$P]-dATP was removed from the labeled oligonucleotide using ProbeQuant G-50 Microcolumns (Amersham) followed by ethanol precipitation. Prior to applying the sample on G-50 microcolumns, sodium acetate was exchanged for the buffer supplied by the manufacturer by one 300-μL wash with 3 M sodium acetate, pH 7 followed by two 300-μL water washes. This step was important because components in the supplied buffer (150 mM NaCl, 10 mM Tris-HCl, pH 8, 1 mM EDTA, and 0.15% Kathon CG/ICP Biocide preservative) decrease the amount of immobilized DNA. Radiolabeled-DNA-modified electrodes were exposed on a phosphorimager screen overnight and scanned using Storm 840 system (Molecular Dynamics). Quantification was performed in the ImageQuaNT software (Molecular Dynamics) by performing volume integration of the equal-area squares drawn around electrodes.

Voltammetry. Cyclic voltammograms were collected using an EG&G Princeton Applied Research 273A potentiostat/galvanostat with a single compartment cell (Willit and Bowden (1990) *J. Phys. Chem.* 94:8241–8246) equipped with a tin-doped indium oxide (ITO) working electrode with a geometric area of 0.32 cm$^2$ (Delta Technologies), Pt-wire auxiliary electrode, and a Ag/AgCl reference electrode (Cypress Systems). Voltammograms of DNA-modified electrodes were taken from 0 to 1.3 V at 10 V/sec in the presence of 25 μM solution of each of the metal complexes in 50 mM sodium phosphate, pH 7. Voltammograms of buffer alone on clean ITO electrodes without DNA were used for background subtraction.

EXAMPLE 2

Experimental Results

Figure 2:
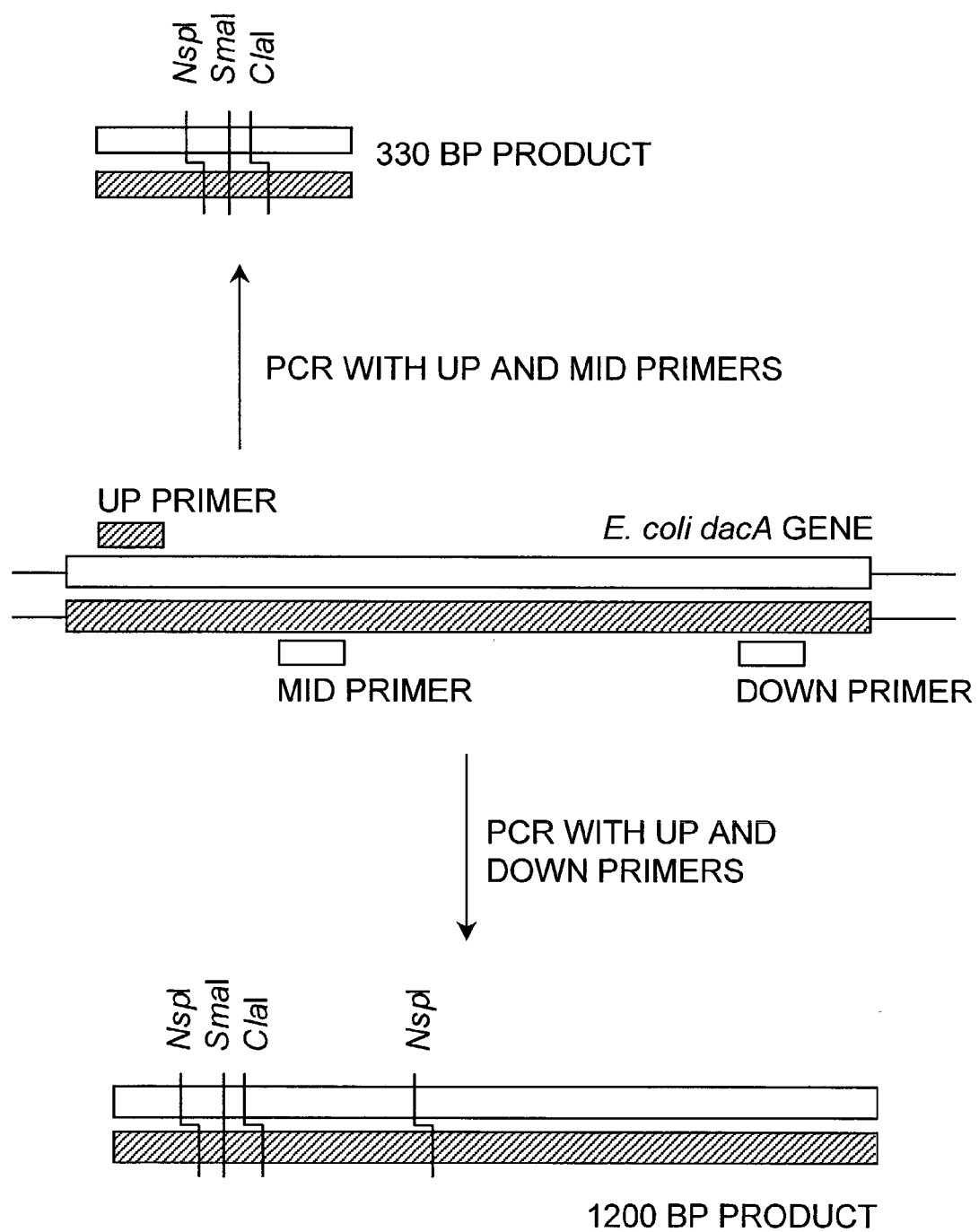
FIG. 2 shows a schematic representation of the strategy used to generate 330 and 1200 base pair PCR products using *E. coli* dacA gene as the template. Primer sequences: CAT GAA TAC CAT TTT TTC CGC TC (up; base pairs 242–264), CGG GTT ACC GGT GGC CCA T (mid; base pairs 554–572), and TTT AAC CAA ACC AGT GAT GGA ACA TT (down, base pairs 1430–1455). Also are shown approximate positions of SmaI, ClaI, and NspI restriction sites.

Polymerase Chain Reaction. The *E. Coli* dacA gene encoding for the penicillin binding protein 5 (PBP5) (GenBank accession number D90703) was used as the template for the polymerase chain reaction with two sets of primers. Amplification with up and mid primers yielded a 330 bp fragment, and a 1200 bp product was generated with a combination of up and down primers (FIG. 2). Eight PCR products synthesized using this strategy are listed in Table 1. Native guanine and adenine are replaced by their 7-deaza analogs in the ratio of 3:1 of the 7-deaza to the unsubstituted purine in PCR products 2, 4, 6, and 8 (Table 1). It has been shown in earlier studies that this ratio affords PCR products in yields comparable to those with native purines (McConlogue et al. (1988) *Nucleic Acids Res.* 16:9869; Seela and Rolling (1992) *Nucleic Acids Res.* 20:55–61). Complete replacement of native guanines or adenines by 7-deaza lesions was possible, as in the case of PCR products 3 and 5 (Table 1), but the yields suffered greatly. The yield loss was in agreement with previous reports (McConlogue et al. (1988) *Nucleic Acids Res.* 16:9869; Seela and Roling (1992) *Nucleic Acids Res.* 20:55–61).

TABLE 1

| PCR Product | Length, bp | Purine Nucleotide Composition[a] |
|---|---|---|
| 1 | 330 | A and G |
| 2 | 330 | A and 3:1 zG:G |
| 3 | 330 | A and zG |
| 4 | 330 | 3:1 zA:A and G |
| 5 | 330 | zA and G |
| 6 | 330 | 3:1 zA:A and 3:1 zG:G |
| 7 | 1200 | A and G |
| 8 | 1200 | A and 3:1 zG:G |

[a] zA = 7-deazaadenine; zG = 7-deazaguanine.

The majority of restriction endonucleases do not cleave the DNA backbone when 7-deazaguanine or 7-deazaadenine is incorporated into the recognition sequence (Grime et al. (1991) *Nucleic Acids Res.* 19:2791; Seela and Roling (1992) *Nucleic Acids Res.* 20:55–61). It has been postulated that this protection from hydrolysis results from an alteration in the local conformation of the DNA duplex at the modified site (Seela and Roling (1992) *Nucleic Acids Res.* 20:55–61). Another possibility is that the enzyme has decreased affinity for DNA containing the modified lesion because contacts with N7 of guanine or adenine are important for recognition (Seela and Roling (1992) *Nucleic Acids Res.* 20:55–61). Protection from hydrolysis at 7-deaza purine sites can be used as a tool to check for incorporation of the modified lesion into the PCR product.

Figure 3:
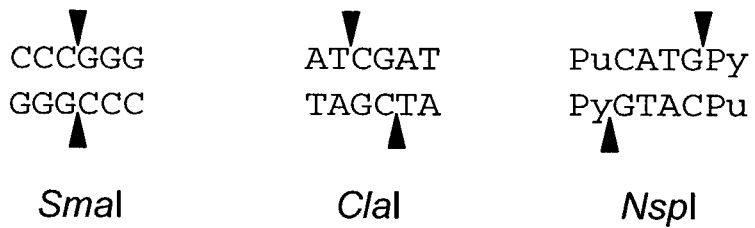
FIG. 3A shows the recognition sequences of restriction endonucleases SmaI, ClaI, and NspI.
FIG. 3B shows the restriction digests of PCR product 1. Lanes: 1, φX 174/HaeIII DNA ladder; 2, no restriction enzyme; 3, SmaI; 4, ClaI; 5, NspI.
FIG. 3C shows the restriction digests of PCR product 2. Lanes: 1, φX 174/HaeIII DNA ladder; 2, no restriction enzyme; 3, SmaI; 4, ClaI; 5, NspI.
FIG. 3D shows the restriction digests of PCR product 4. Lanes: 1, φX 174/HaeIII DNA ladder; 2, no restriction enzyme; 3, SmaI; 4, ClaI; 5, NspI.
FIG. 3E shows the restriction digests of PCR product 6. Lanes: 1, φX 174/HaeIII DNA ladder; 2, no restriction enzyme; 3, SmaI; 4, ClaI; 5, NspI.
Figure 3:
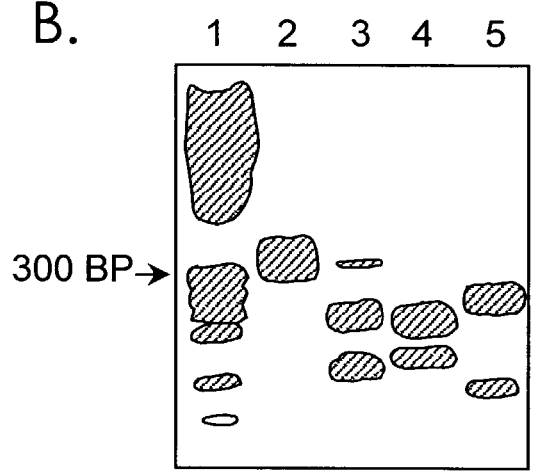
Figure 3:
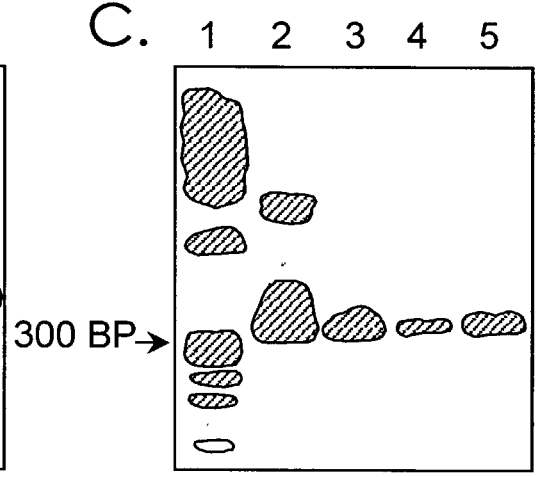
Figure 3:
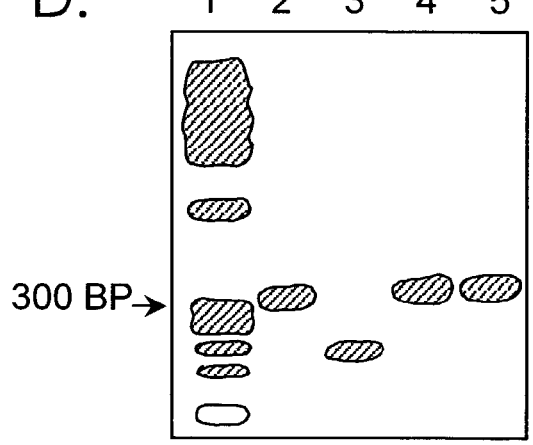
Figure 3:
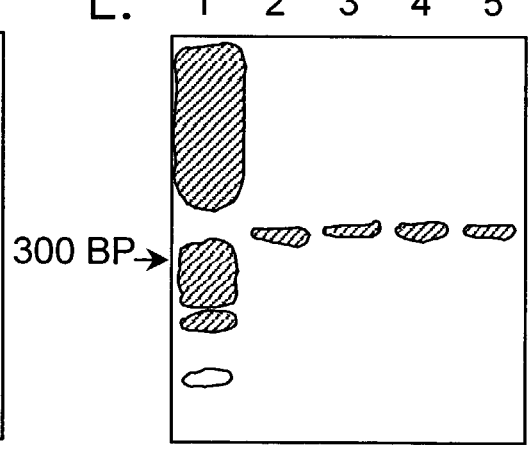

The approximate positions of the restriction sites for the enzymes SmaI, ClaI, and NspI are shown schematically in FIG. 2. Digestion of both 330 and 1200 bp PCR products containing native purines should result in shorter fragments that can be separated on a gel from the full-size product expected for digests of PCR products containing the modified lesions. Protection of the DNA backbone from cleavage by all three enzymes was anticipated for 7-deazaguanine because all three endonucleases have guanine in their recognition sequences (FIG. 3A). On the other hand, adenine is not in the recognition sequence of SmaI (FIG. 3A), so PCR products containing 7-deazaadenine should be cleaved by this endonuclease but protected from hydrolysis by ClaI and NspI.

Restriction digests were performed on all eight PCR products synthesized in the present study (Table 1), and the representative digests are shown in FIGS. 3B–E. Complete DNA cleavage by all three enzymes was seen for PCR product 1, which contained native guanines and adenines (FIG. 3B). As expected, the 7-deazaguanine-containing PCR product 2 was protected from digestion by all three endonucleases (FIG. 3C) while PCR product 4, which contained 7-deazaadenine, was cleaved by SmaI only (FIG. 3D). Finally, PCR product 6 contains both 7-deazapurines and was only hydrolyzed to a small extent by SmaI (FIG. 3E). The restriction digests therefore provide direct evidence of incorporation of the modified lesions into the PCR products.

DNA Immobilization. Immobilization of the PCR products was achieved by direct attachment of the nucleic acid to the ITO surface via the interaction of the phosphate backbone with the metal oxide (Armistead, P. M.; Thorp, H. H. *Anal. Chem.* 2000, 72, 3764–3770.)). DNA was precipitated from the 9:1 solution of dimethylformamide (DMF) and 100 mM sodium acetate, pH 6.8 by incubation in a constant humidity chamber for a controlled amount of time. Extensive washing with water and salt removes excess DNA that was not immobilized strongly on the surface. Oxidation of guanine in oligonucleotides and polymers of DNA (Armistead, P. M.; Thorp, H. H. *Anal. Chem.* 2000, 72,3764–3770).

Individual PCR Products. The extent of the ITO surface modification was determined by phosphorimagery of the electrodes that were exposed to radiolabeled PCR products. The amounts of immobilized nucleic acid along with the immobilization efficiencies of individual PCR products determined from the amount of DNA applied to the electrode surface are summarized in Table 2. One-hour incubation afforded 20–30% immobilization efficiency regardless of purine nucleotide composition and DNA length. The presence of modified bases was not expected to affect the extent of electrode modification since nucleic acid strands interact with the metal oxide surface through the phosphate backbone. This result was of special significance because it allowed for direct comparison of current enhancements in cyclic voltammetry for different modified DNA bases without the need for normalization to the amount of immobilized nucleic acid.

TABLE 2

| PCR Product | Incubation time, hrs | Amount of PCR product immobilized, pmol nucleotide[a] | Immobilization efficiency, %[b] |
|---|---|---|---|
| 1 | 1 | 160 ± 8.2 | 21 |
| 4 | 1 | 190 ± 10 | 25 |
| 7 | 1 | 200 ± 20 | 27 |
| 8 | 1 | 180 ± 24 | 24 |
| 1 | 4 | 380 ± 24 | 51 |
| 4 | 4 | 360 ± 9.8 | 48 |
| 6 | 4 | 350 ± 22 | 47 |

[a]Each reported value was an average with one standard deviation of three electrodes.
[b]Based on 750 pmol nucleotide applied to the surface.

The DNA length did not appear to influence the immobilization efficiency for relatively short incubation times. Longer fragments have more phosphate groups on each individual strand and therefore should bind to the metal oxide with a higher affinity. On the other hand, larger number of shorter fragments may be immobilized because they occupy a smaller area on the electrode surface. Apparently, these two opposing effects counteract each other during the one-hour incubation, resulting in similar extents of electrode modification by DNA molecules of different sizes.

An increase in the incubation time from one to four hours resulted in an increase in the immobilization efficiency from 20–30% to 50% for the 330 bp DNA fragments (Table 2). The increase was not linear, which was in agreement with kinetic investigations of this system that show a saturation in the amount of immobilized DNA during the time course of the reaction (Armistead, P. M.; Thorp, H. H. *Anal. Chem.* 2000, 72, 3764–3770). As in the case of shorter incubation time, purine nucleotide composition of the PCR product did not influence the amount of nucleic acid bound to the ITO surface.

Mixtures of PCR Products. 330 and 1200 bp PCR products were co-immobilized on the ITO surface and the extents of electrode modifications by each of the two components determined by phosphorimagery (Table 3). Electrodes were exposed to mixtures of the two fragments either at the identical nucleotide or strand concentration. 1200 bp fragments showed an enhanced affinity for the ITO surface relative to 330 bp PCR products due to the presence of more phosphate groups on each individual DNA strand. The immobilization efficiency of the 330 bp PCR products 1 and 4 decreased when the amount of nucleotide applied to the electrode was decreased to make the strand concentrations of the 330 and 1200 bp fragments equal. The decrease in the amount of the shorter fragment attached to the ITO surface was accompanied by a concomitant increase in the immobilization efficiency of the PCR product 8 because more binding sites on the electrode surface became available to the longer PCR product.

TABLE 3

| PCR products | Amount of PCR products applied, pmol nucleotide[a] | Amount of PCR products immobilized, pmol nucleotide[c] | Immobilization efficiency, % |
|---|---|---|---|
| 1 & 8 | 750/750 | 120 ± 26/180 ± 39 | 16/24 |
| 4 & 8 | 750/750 | 130 ± 23/230 ± 24 | 17/31 |
| 1 & 8 | 200/720[b] | 21 ± 5.3/250 ± 24 | 11/35 |
| 4 & 8 | 200/720[b] | 21 ± 4.0/270 ± 24 | 11/38 |

[a]Incubation time was 1 hour.
[b]200 and 720 pmol nucleotide corresponds to 30 fmol strand for 330 bp and 1200 bp products, respectively.
[c]Each reported value was an average with one standard deviation of three electrodes Voltammetry. Electrochemical detection of 7-deazapurine lesions incorporated into the PCR products was achieved by mediated cyclic voltammetry. Voltammograms of mixtures of metal complex mediators with different redox potentials were collected on DNA-modified ITO electrodes at high scan rates. High scan rates were essential in the case when DNA was immobilized on the electrode surface and catalyst was in solution for reasons that have been discussed in detail elsewhere (Armistead (2000) The catalytic oxidation of guanine adsorbed to indium tin oxide. In Chemistry (Chapel Hill, NC: University of North Carolina at Chapel Hill); Armistead and Thorp (2000) *Anal. Chem.* In press).

PCR Products with 7-Deazaguanine. ITO electrodes modified with 330 bp PCR products containing guanine (1), 3:1 7-deazaguanine:guanine (2), and 7-deazaguanine (3) were used in the initial set of voltammetry studies. Representative voltammograms of an equimolar mixture of $Fe(bpy)_3^{3+/2+}$ ($E_{1/2}$=0.83 V vs. Ag/AgCl) and $Ru(bpy)_3^{3+/2+}$ ($E_{1/2}$=1.05 V vs. Ag/AgCl) on DNA-modified electrodes are shown in FIG. 4A. As expected, a large current enhancement was observed in the $Ru(bpy)_3^{2+}$ wave in the presence of PCR product 1 due to catalytic oxidation of guanine by the metal complex. A small current enhancement in the $Fe(bpy)_3^{3+/2+}$ peak reflects a slow rate constant for oxidation of guanine by the complex with a lower redox potential.

Replacement of native guanines by 7-deaza analogs in PCR products 2 and 3 resulted in a small increase in the oxidative wave of iron. $Fe(bpy)_3^{3+/2+}$ was a sufficiently powerful oxidant to react with 7-deazaguanine lesions ($E_{1/2}$=0.75 V) (Kelley and Barton (1998) *Chem. Biol.* 5:413–425; Yang, I. V.; Thorp, H. H. *Inorg. Chem.* 2001, 40, 1690–1697.) to an appreciable extent. In fact, the reaction of Ru(Me$_2$bpy)$_3^{3+/2+}$, whose redox potential ($E_{1/2}$=0.86 V) was similar to that of Fe(bpy)$_3^{3+/2+}$, with 7-deazaguanines in oligonucleotides was fast both with oligonucleotides in solution and immobilized on the electrode surface. Since the number of zG lesions immobilized on the electrode surface was comparable for oligonucleotides and PCR products, it appears that the reactivity of 7-deazaguanine was diminished in immobilized DNA polymers compared to oligonucleotides. The decreased current enhancement in this study could also be due to the decomposition of the catalyst. Oxidized complexes of iron are inherently less stable than those of ruthenium, and the self-oxidation process may be catalyzed by the presence of the nucleic acid; binding to the polyanion increases the local concentration of the metal complex and may promote the decomposition. It has been previously shown that disproportionation of RuOH$^{2+}$ complexes to RuO$^{2+}$ and RuOH$_2^{2+}$ forms was enhanced in the presence of polymeric DNA (Welch et al. (1997) *Inorg. Chem.* 36:812–4821).

The increase in the current in the iron wave upon the replacement of guanines by 7-deazaguanines is accompanied by a large decrease in the peak current for Ru(bpy)$_3^{3+/2+}$. This reduced current enhancement is due to the decrease in the number of guanines as they are replaced by 7-deaza analogs. The residual current enhancement in the ruthenium wave on electrodes modified with the PCR product containing no native guanines is probably due to the incomplete reaction of iron with 7-deazaguanine, leaving some zG lesions available to react with ruthenium. This result is similar to our observations of residual reactivity of 7-deazaguanine with Ru(bpy)$_3^{33+/2+}$ after the reaction with Ru(Me$_2$bpy)$_3^{3+/2+}$ in oligonucleotides containing multiple zG bases.

A histogram of average peak currents for the two metal complexes from three sets of independent experiments is plotted in FIG. 4B. Although the current enhancement in the Fe(bpy)$_3^{3+/2+}$ wave became more pronounced as more zG lesions were incorporated into the PCR product, the peak currents for the PCR products 1, 2, and 3 were within the error of each other. To increase the reproducibility, a 1200 bp PCR product was synthesized with either native guanines (7) or 75% 7-deazaguanines (8). The PCR product containing all 7-deazaguanines was excluded from this study because the amplification of the 1200 bp portion of template DNA in the presence of all 7-deaza-dGTP was inefficient. The presence of a larger number of zG lesions in longer DNA polymers may result in more current enhancement. Fe(bpy)$_3^{2+}$ was also replaced with Ru(Me$_2$bpy)$_3^{2+}$ to alleviate any problems associated with catalyst decomposition.

Figure 4:
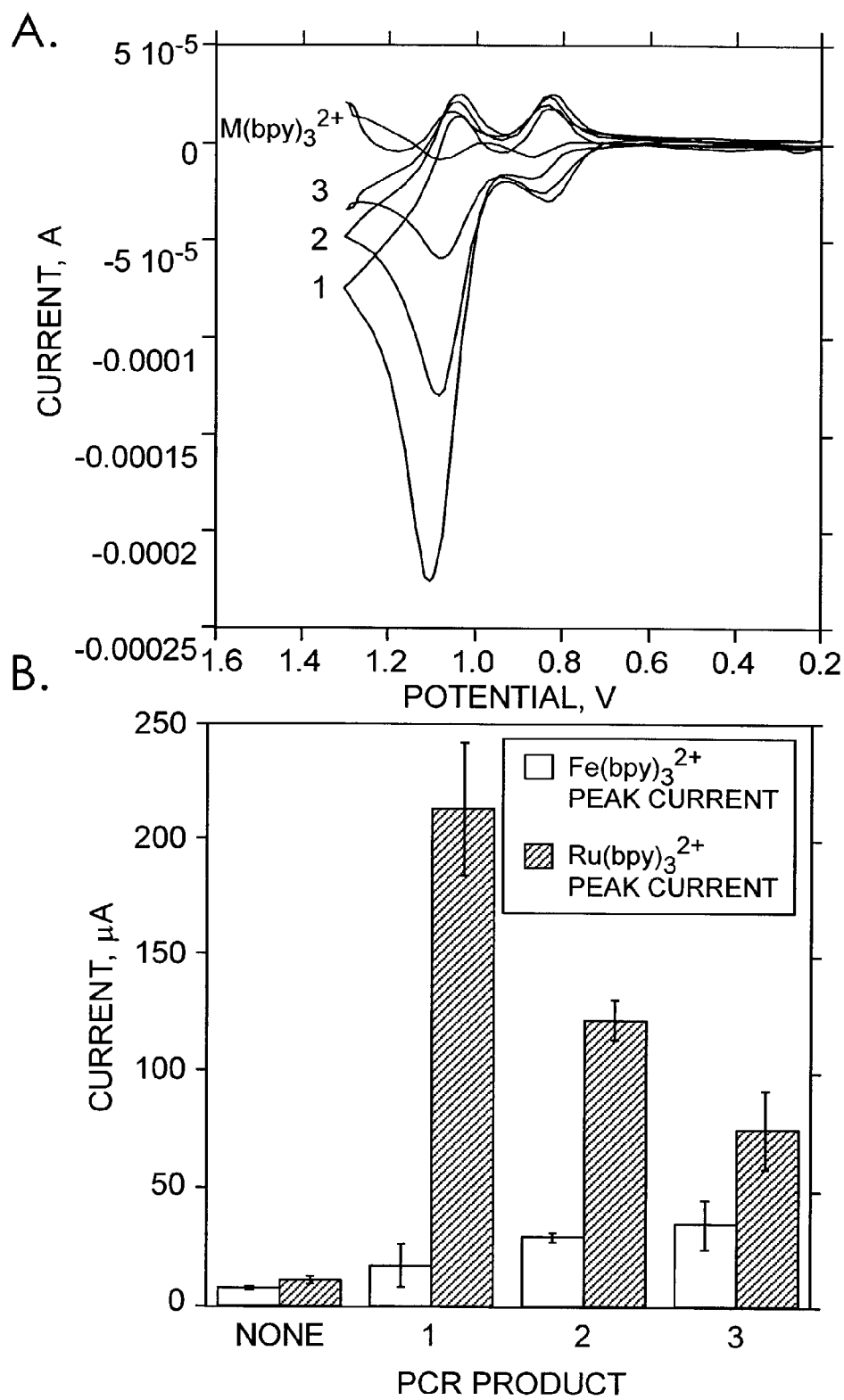
FIG. 4A shows cyclic voltammograms of 25 μM Fe$(bpy)_3^{2+}$ and Ru$(bpy)_3^{2+}$ on unmodified and DNA-modified ITO electrodes collected at 10 V/sec in 50 mM sodium phosphate, pH 7. ITO surface was modified with 750 pmol of PCR products 1, 2, or 3 (see Table 1 for nomenclature)
FIG. 4B shows a histogram of average peak currents for the two metal complexes from three independent experiments. Error bars represent one standard deviation.

Representative voltammograms of Ru(Me$_2$bpy)$_3^{2+}$ and Ru(bpy)$_3^{2+}$ taken on ITO electrodes modified with PCR products 7 or 8 are shown in FIG. 5A, and the histogram of average peak currents for the two metal complexes from three sets of independent experiments is plotted in FIG. 5B. The trends in current enhancements in the oxidative waves of Ru(Me$_2$bpy)$_3^{3+/2+}$ and Ru(bpy)$_3^{3+/2+}$ were similar to those of the 330 bp fragments (FIG. 4). However, larger and more reproducible peak currents were observed for the 1200 bp PCR products due to the higher concentration of reactive nucleotides on the ITO surface. Thus, 7-deazaguanine lesions can be reproducibly detected by Ru(Me$_2$bpy)$_3^{3+/2+}$ in longer DNA polymers. It is advantageous that the overall current and reproducibility increase for larger DNA molecules because the majority of biologically relevant sequences are at least 1 kb long.

PCR Products with 7-Deazaadenine. Cyclic voltammograms of an equimolar mixture of Fe(bpy)$_3^{2+}$ and Ru(bpy)$_3^{2+}$ were taken on ITO electrodes modified with 330 bp PCR fragments containing adenine (1), 3:1 7-deazaadenine:adenine (4), and 7-deazaadenine (5) (FIG. 6A). Current enhancement in the ruthenium peak on electrodes modified with the PCR product 1 was due to the catalytic oxidation of guanines. When zA lesions were introduced into the DNA polymer, current enhancement in the ruthenium wave became more pronounced because Ru(bpy)$_3^{3+/2+}$ was capable of oxidizing 7-deazaadenines (Baik et al., *J. Phys. Chem. B* (2001) in press) in addition to guanines. The redox potential of Fe(bpy)$_3^{3+/2+}$ was not high enough to effect the oxidation of 7-deazaadenine, resulting in no current enhancement in the iron wave. Larger number of 7-deazaadenine lesions in the PCR product 5 relative to 4 does not lead to more current, which is indicative of a saturation in current response. This is analogous to the reaction of native guanines with Ru(bpy)$_3^{3+/2+}$, where current saturates as the concentration of immobilized guanine is increased (Armistead and Thorp (2000) *Anal. Chem.* In press).).

Two factors probably contribute to the enhanced reactivity of DNA molecules containing both G and zA nucleobases. One is the increase in the number of reactive sites, which is in effect an increase in the substrate concentration. The other possible contributor is the decreased distance between reactive sites. It is well established that radical cations that result from one-electron oxidation of guanine can migrate in DNA over relatively short distances (Bixton et al. (1999) *Proc. Natl. Acad. Sci. USA.* 96:11713–11716; Henderson et al. (1999) *Proc. Natl. Acad. Sci.* 96:8353–8358). Increased interaction between reactive guanine and 7-deazaadenine sites through charge migration along the DNA axis may lead to more pronounced current enhancements observed for DNA molecules containing both lesions.

The histogram of the average peak currents from three sets of electrodes (FIG. 6B) clearly demonstrates that 7-deazaadenine lesions can be reproducibly detected by more pronounced current enhancement in the Ru(bpy)$_3^{3+/2+}$ wave relative to the current due to native guanine nucleobases. Since current enhancements are fairly large and appear to reach saturation, the effect of a decrease in the amount of DNA applied on the ITO surface was investigated. Representative voltammograms of Ru(Me$_2$bpy)$_3^{2+}$ and Ru(bpy)$_3^{2+}$ taken on ITO electrodes modified with 210 pmol of PCR products 1 or 4 are shown in FIG. 7A, and the histogram of average peak currents for the two metal complexes from three sets of independent experiments is plotted in FIG. 7B. As expected, current enhancements in the Ru(bpy)$_3^{3+/2+}$ peak decrease in magnitude, but, more importantly, PCR products with no 7-deazadenine and 75% 7-deazaadenine can be easily distinguished even at the reduced concentration of the substrate.

PCR Product with 7-Deazaadenine and 7-Deazaguanine. Initial studies on simultaneous detection of 7-deazaguanine and 7-deazaadenine were performed on the PCR product 6, in which 75% of native purines were replaced by their 7-deaza analogs. One-hour incubation of ITO electrodes with 750 pmol nucleotide DNA resulted in an appreciable current enhancement in the Ru(bpy)$_3^{3+/2+}$ wave due to the oxidation of 7-deazaadenines and native guanines, but no current enhancement was observed in the Ru(Me$_2$bpy)$_3^{3+/2+}$ peak (data not shown). This observation was consistent with the results on 330 bp fragments containing 7-deazaguanine (2 and 3) where current enhancements in the $Fe(bpy)_3^{3+/2+}$ peak were small (FIG. 4). To increase the concentration of zG lesions, an attempt was made to make a 1200 bp PCR product containing both 7-deazapurines, but the synthesis of this fragment was difficult and inefficient. Instead, an increased concentration of immobilized 7-deazaguanine was achieved by increasing the incubation time for PCR product 6 from one to four hours. Longer incubation time resulted in the increase in the immobilization efficiency from 20–30% to 50% (Table 2), which should in turn lead to larger current enhancements.

Figure 8:
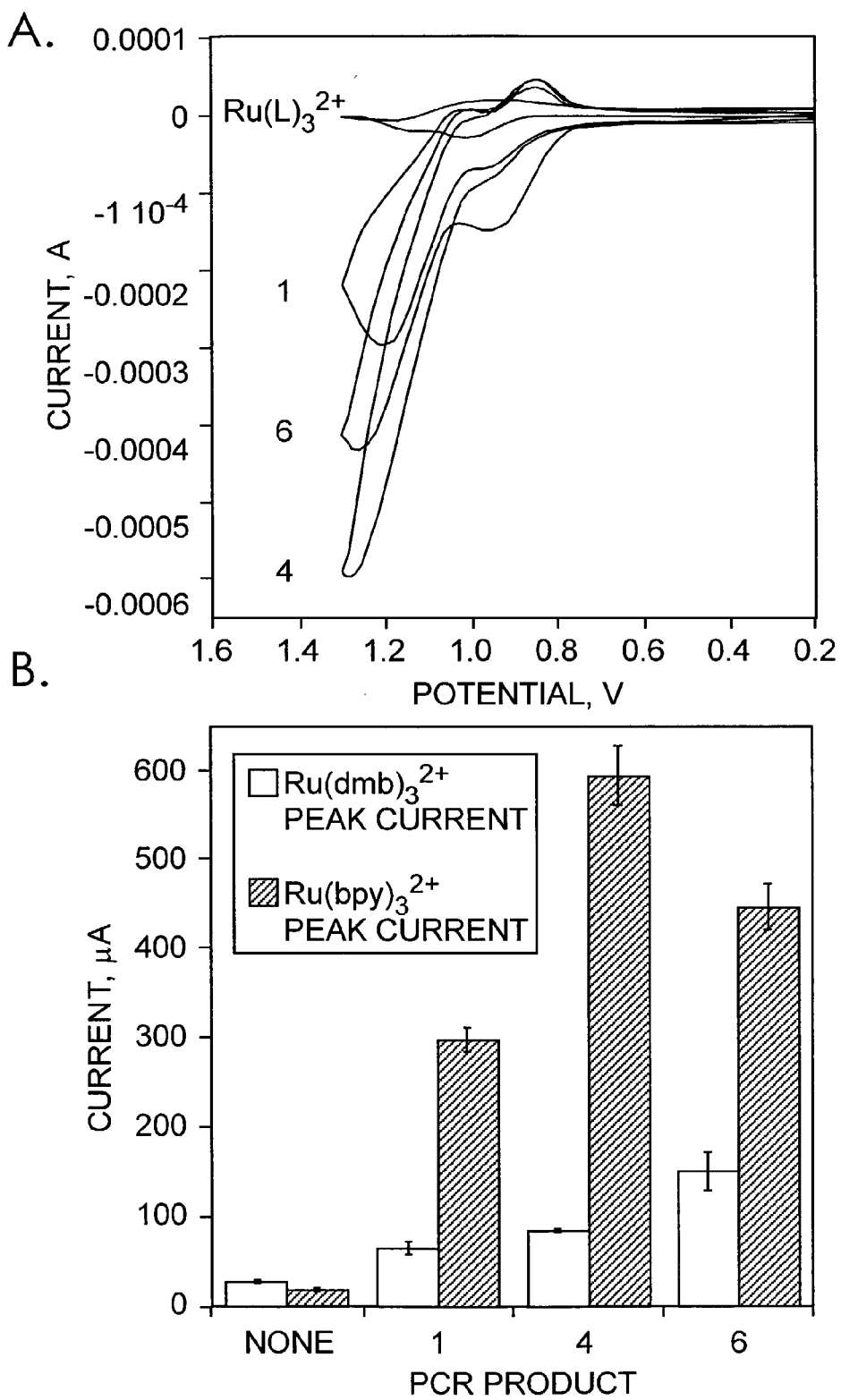
FIG. 8A shows cyclic voltammograms of 25 μM Ru$(Me_2bpy)_3^{2+}$ and Ru$(bpy)_3^{2+}$ on unmodified and modified ITO electrodes collected at 10 V/sec in 50 mM sodium phosphate, pH 7. Electrodes were incubated for 4 hours with 750 pmol PCR products 1, 4, or 6 (see Table 1 for nomenclature).
FIG. 8B shows a histogram of average peak currents with one standard deviation for the two metal complexes determined in three independent experiments.

A representative set of cyclic voltammograms of $Ru(Me_2bpy)_3^{2+}$ and $Ru(bpy)_3^{2+}$ taken on ITO electrodes modified with PCR products 1, 4, or 6, and a histogram of average peak currents from three independent measurements are shown in FIG. 8. Longer incubation time resulted in more pronounced current enhancements and allowed for simultaneous detection of 7-deazaguanine and 7-deazaadenine in the 330 bp fragment 6. As in the case of PCR products containing one of the modified lesions, the presence of 7-deazaguanine was detected by current enhancement in the $Ru(Me_2bpy)_3^{3+/2+}$ peak current while 7-deazaadenine produced more pronounced current enhancement in the $Ru(bpy)_3^{3+/2+}$ wave relative to the PCR product containing native guanines only (1). Very little background current due to residual oxidation of G and zA was seen in the $Ru(Me_2bpy)_3^{3+/2+}$ peak even at these higher concentrations of guanine and 7-deazaadenine (PCR products 1 and 4).

Figure 5:
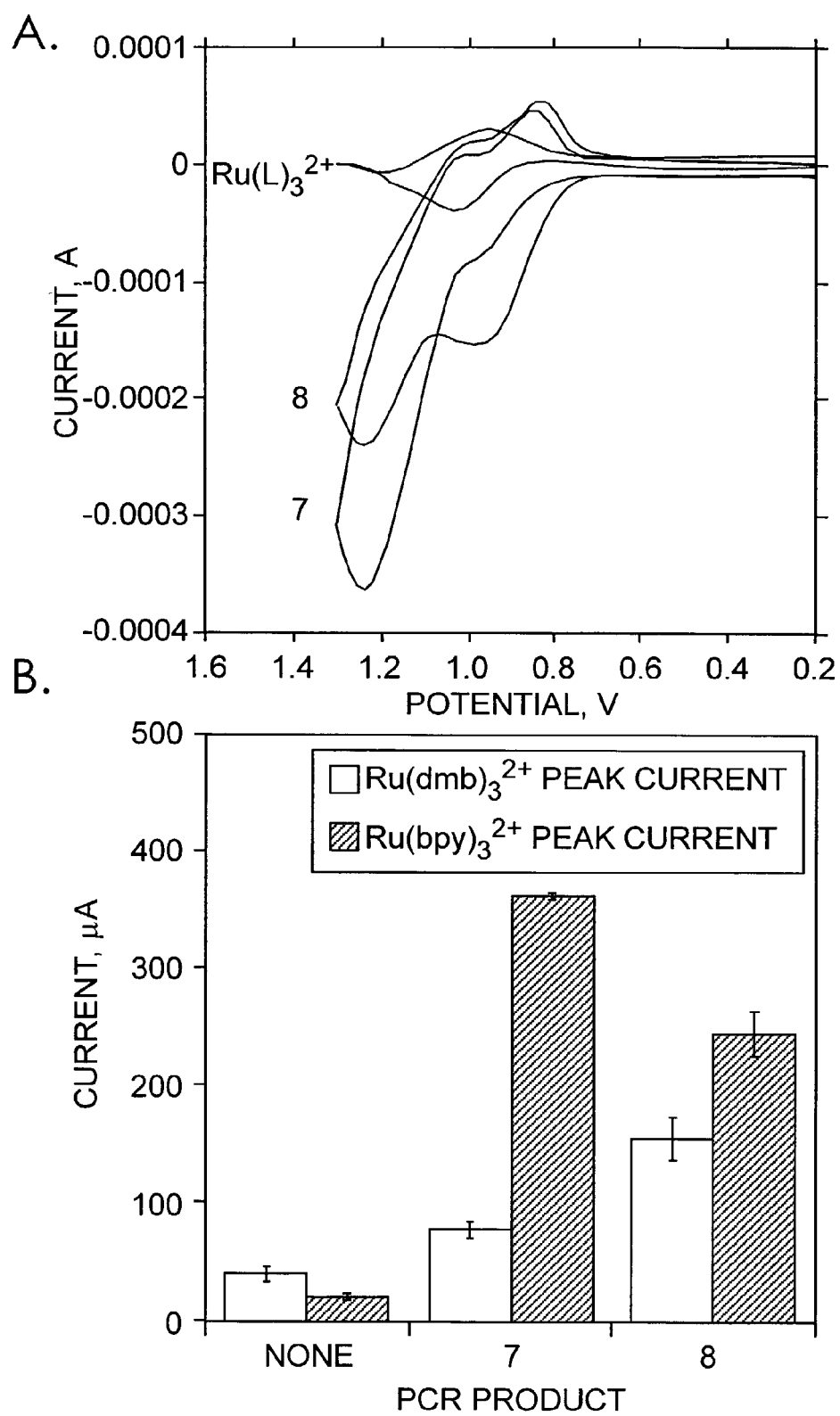
FIG. 5A shows cyclic voltammograms of 25 μM Ru$(Me_2bpy)_3^{2+}$ and Ru$(bpy)_3^{2+}$ on ITO electrodes modified with no DNA, or 750 pmol PCR products 7, or 8 (see Table 1 for nomenclature). Voltammograms were taken at 10 V/sec in 50 mM sodium phosphate, pH 7.
FIG. 5B shows a histogram of average peak currents with one standard deviation for the two metal complexes determined in three independent experiments.
Figure 6:
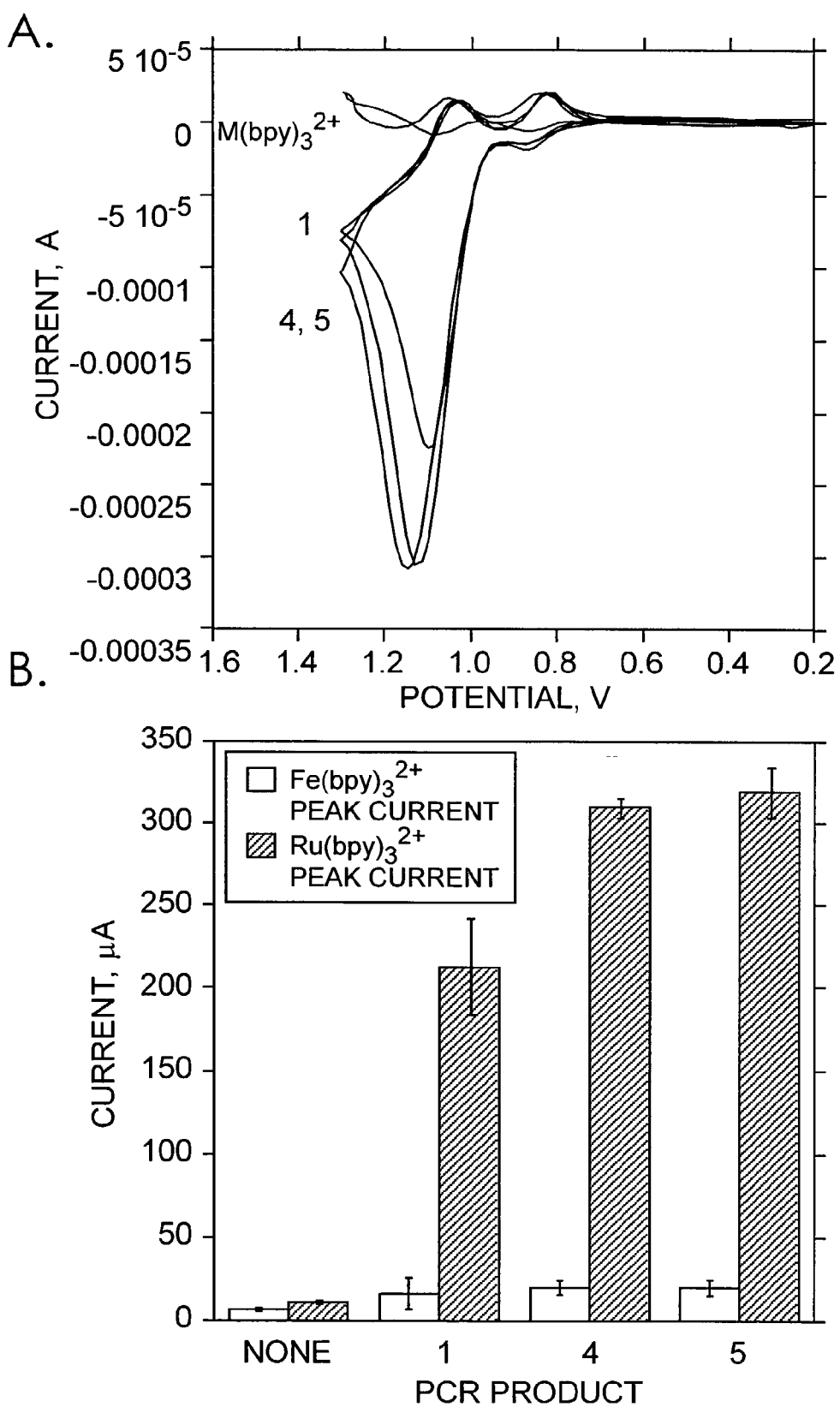
FIG. 6A shows cyclic voltammograms of 25 μM Fe$(bpy)_3^{2+}$ and Ru$(bpy)_3^{2+}$ on unmodified and DNA-modified ITO electrodes collected at 10 V/sec in 50 mM sodium phosphate, pH 7. ITO surface was modified with 750 pmol of PCR products 1, 4, or 5 (see Table 1 for nomenclature)
FIG. 6B shows a histogram of average peak currents for the two metal complexes from three independent experiments. Error bars represent one standard deviation.
Figure 7:
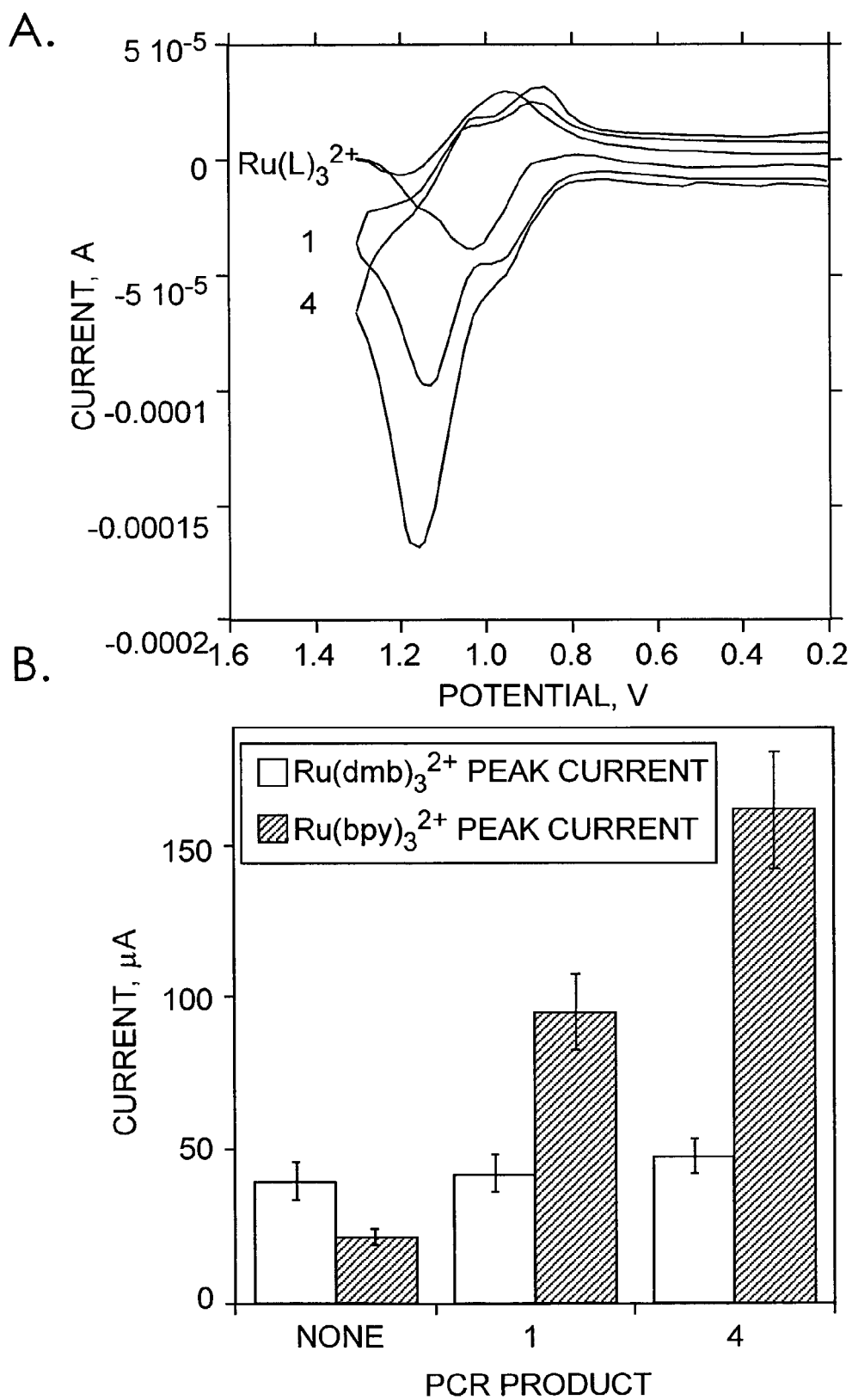
FIG. 7A shows cyclic voltammograms of 25 μM Ru$(Me_2bpy)_3^{2+}$ and Ru$(bpy)_3^{2+}$ on ITO electrodes modified with no DNA, or 210 pmol PCR products 1, or 4 (see Table 1 for nomenclature). Voltammograms were taken at 10 V/sec in 50 mM sodium phosphate, pH 7.
FIG. 7B shows a histogram of average peak currents with one standard deviation for the two metal complexes determined in three independent experiments.

Mixtures of PCR Products. Simultaneous detection of multiple DNA sequences was achieved by co-immobilization of PCR products containing 7-deaza analogs of guanine and adenine and subsequent voltammetry with a mixture of $Ru(Me_2bpy)_3^{2+}$ and $Ru(bpy)_3^{2+}$, as represented schematically in FIG. 1A. 1200 bp fragment having 75% zG (8) was co-immobilized with a 330 bp polynucleotide containing no modified bases (1) or 75% zA (4). Products 8 and 4 were chosen because it has already been shown that 7-deazaguanine and 7-deazaadenine can be detected with good sensitivity and selectivity in these two DNA molecules, respectively (FIGS. 5, 6, and 7). PCR product 1 was included in the study as a control for the background current due to the oxidation of native guanines.

Figure 9:
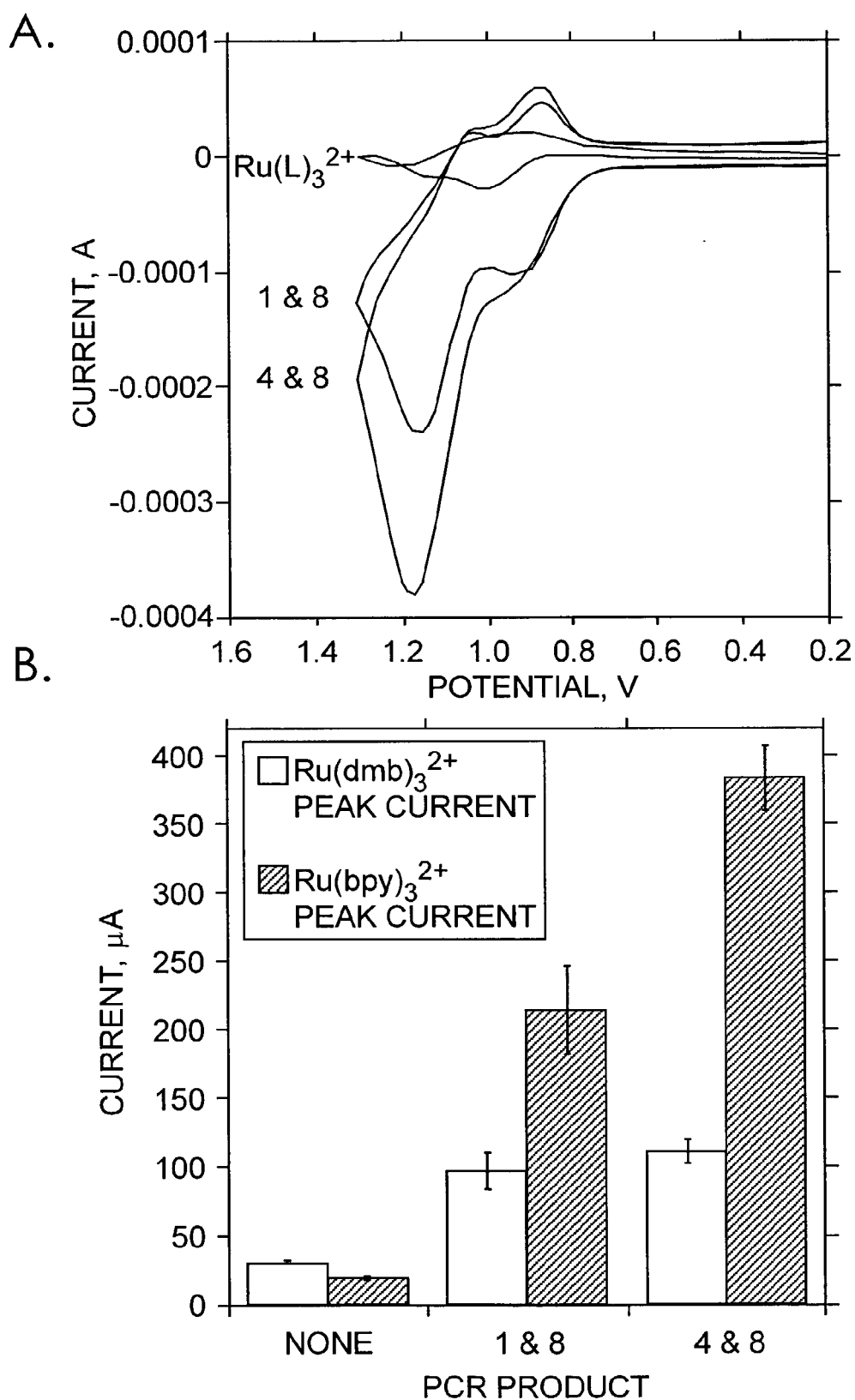
FIG. 9A shows representative cyclic voltammograms of 25 μM Ru$(Me_2bpy)_3^{2+}$ and Ru$(bpy)_3^{2+}$ on ITO electrodes modified with no DNA or mixtures of PCR products. PCR product 8 was co-immobilized with PCR product 1 or 4 at the same nucleotide quantity (750 pmol) (see Table 1 for PCR product nomenclature). Voltammograms were taken in 50 mM sodium phosphate, pH 7 at 10 V/sec.
FIG. 9B shows a histogram of the average peak currents with one standard deviation for the two metal complexes determined on three sets of electrodes.

In the first set of experiments, the ITO surface was modified with mixtures of the two DNA sequences at the same nucleotide quantity (750 pmol). Cyclic voltammograms of $Ru(Me_2bpy)_3^{2+}$ and $Ru(bpy)_3^{2+}$ taken on these electrodes clearly demonstrated that incorporation of zG and zA in PCR products enabled simultaneous detection of two DNA sequences (FIG. 9). The 1200 bp fragment 8 was detected by selective oxidation of incorporated 7-deazaguanine lesions by $Ru(Me_2bpy)_3^{3+/2+}$. The 330 bp PCR product 4 was detected by an increase in the $Ru(bpy)_3^{3+/2+}$ wave due to oxidation of incorporated 7-deazaadenine lesions in addition to native guanines.

Figure 10:
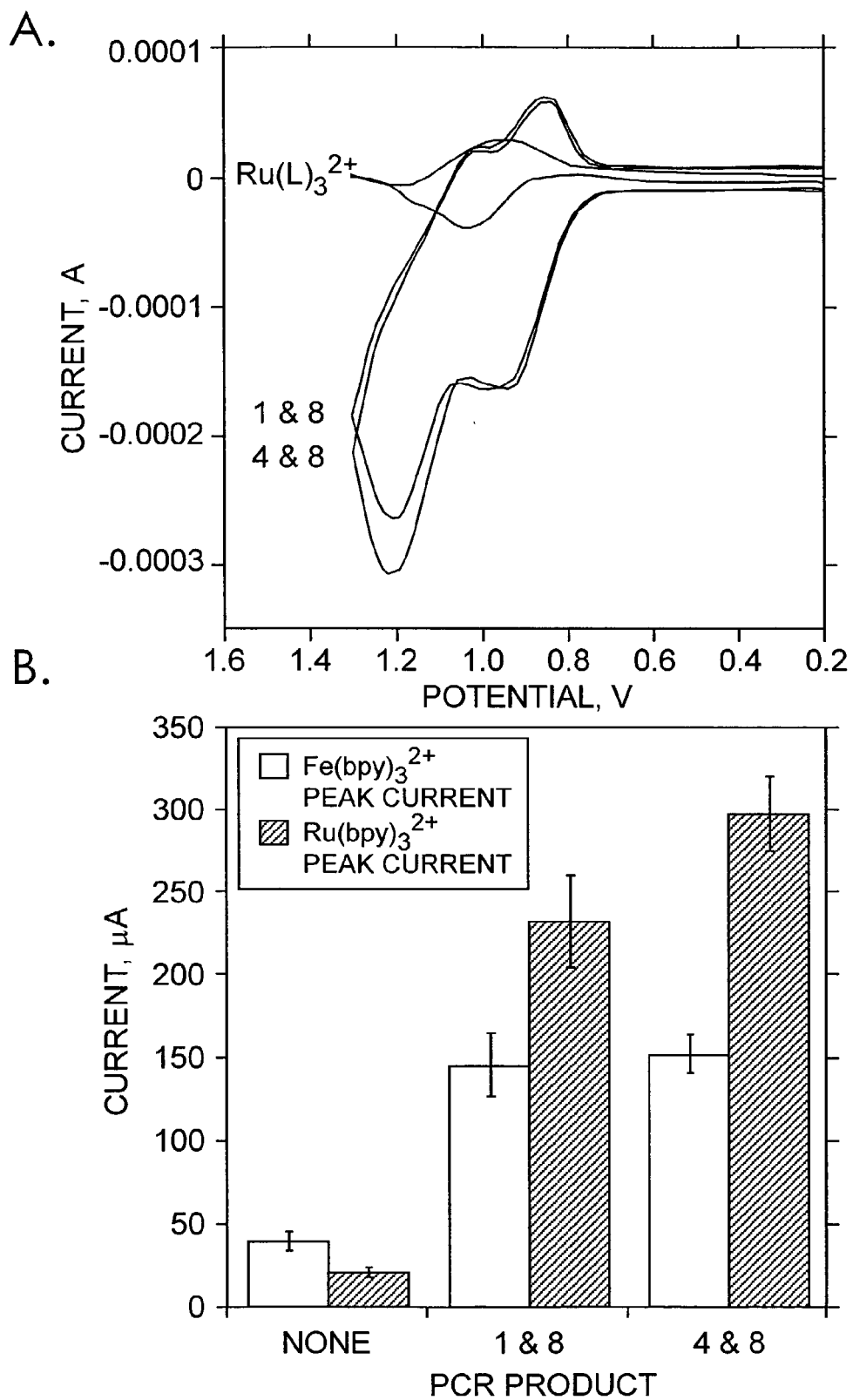
FIG. 10A shows representative cyclic voltammograms of 25 μM Ru$(Me_2bpy)_3^{2+}$ and Ru$(bpy)_3^{2+}$ on ITO electrodes modified with no DNA or mixtures of PCR products. PCR product 8 was co-immobilized with PCR product 1 or 4 at the same strand quantity (30 fmol) (see Table 1 for PCR product nomenclature). Voltammograms were taken in 50 mM sodium phosphate, pH 7 at 10 V/sec.
FIG. 10B shows a histogram of average peak currents with one standard deviation for the two metal complexes determined in three independent experiments.

Alternatively, electrodes were modified with mixtures of DNA molecules at the same strand quantity of 30 fmol, which corresponds to 720 pmol nucleotide of the 1200 bp fragment and 200 pmol nucleotide of the 330 bp PCR products. Phosphorimagery studies showed that changes in relative concentrations of the two fragments resulted in a decrease in the immobilization efficiency for the shorter fragment accompanied by an increase in the amount of the longer PCR product attached to the ITO surface (Table 3). Based on these results, more current enhancement was expected in the $Ru(Me_2bpy)_3^{3+/2+}$ wave because more 7-deazaguanines are immobilized on the electrode, and a decrease in the $Ru(bpy)_3^{3+/2+}$ peak current due to the presence of reduced number of 7-deazaadenines on the ITO surface. Cyclic voltammograms and histograms of peak currents plotted in FIG. 10 show the expected trend. More importantly, the two DNA sequences can be detected with good reproducibility in the same manner as they are detected when they are co-immobilized at the same nucleotide concentration.

EXAMPLE 3

Mismatch Detection

Oligonucleotide 1, its Watson-Crick complement 2, and complements containing mismatches (3, 4, 5) were obtained from the Nucleic Acids Core Facility of the Lineberger Cancer Center at UNC-CH. The oligonucleotide 1 contains a first preselected base, 8-oxoadenine (8OA), that is oxidized by a first mediator, $Fe(bpy)_3^{3+}$. Oligonucleotide 1 also contains a second preselected base, 8-oxoguanine (8OG), that is oxidized by a second mediator, $Os(bpy)_3^{3+}$, and the first mediator, $Fe(bpy)_3^{3+}$.

| Oligo-nucleotide | DNA Sequence (5'→3') |
|---|---|
| 1 | AAA TAT A8OAT ATA ATA 8OGAT AAT AAA |
| 2 | TTT ATT ATC TAT TAT ATT ATA ATA TTT |
| 3 | TTT ATT ATA TAT TAT ATT ATA ATA TTT |
| 4 | TTT ATT ATC TAT TAT AGT ATA ATA TTT |
| 5 | TTT ATT ATA TAT TAT AGT ATA ATA TTT |

Oligonucleotide 1 was ethanol-precipitated twice, and all other oligonucleotides were ethanol-precipitated once before use in electrochemistry experiments. Concentrations of stock solutions of oligonucleotides were determined spectrophotometrically using a Hewlett-Packard 8452A diode-array spectrometer. For electrochemistry experiments, one equivalent of oligonucleotide 1 was hybridized to 1.1 equivalents of oligonucleotides 2–5 by 5 min of heating to 95° C. followed by cooling to room temperature over 2 h. Solutions used for electrochemistry contained 50 μM (strand) oligonucleotide 1, 50 μM of $Os(bpy)_3Cl_2$ and $Fe(bpy)_3Cl_2$, and 50 mM sodium phosphate buffer with 800 mM NaCl at pH 7. Cyclic voltammograms were collected at a scan rate of 25 mV/s. A freshly cleaned ITO electrode was used for each experiment. An initial scan containing 50 mM sodium phosphate buffer with 800 mM NaCl, pH 7 was subtracted from each experimental cyclic voltammogram. ITO electrodes were conditioned for at least four cycles in buffer before the background cyclic voltammogram was collected. At least three experiments were performed for each data point. Digital simulation was performed as described in Johnston 1995 using the Bioanalytical Systems software package Digisim™.

Figure 11:
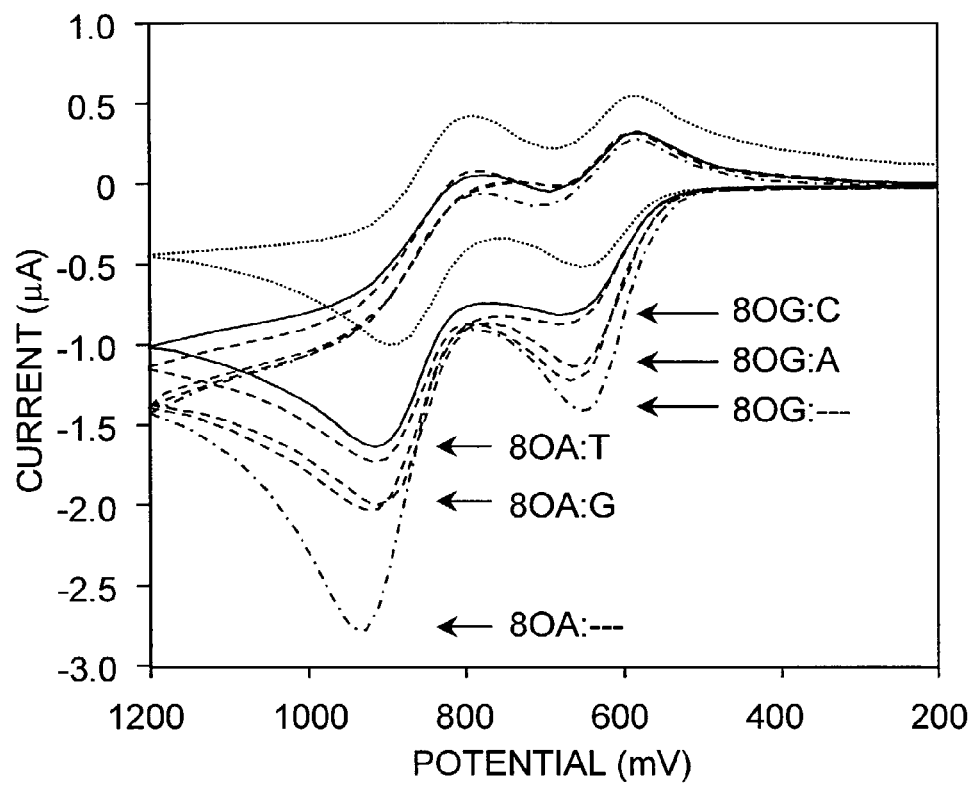
FIG. 11. The dotted line is for the metal complexes alone. Dashed line is for single-stranded 1. Solid line is for 1 hybridized to its exact complement 2. Large dashed lines are for 1 hybridized to oligonucleotides 3–5, which contain 1 or 2 bases that are mismatches to 8-oxo-adenine or 8-oxo-guanine. All cyclic voltammograms were collected at 25 mV/s.
Figure 12:
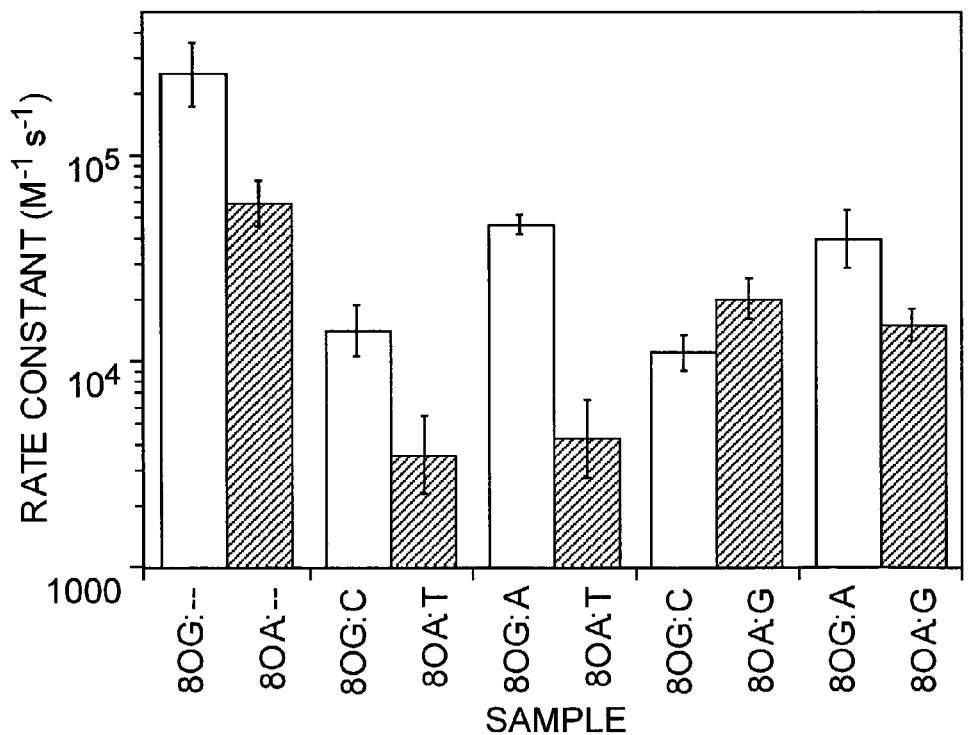
FIG. 12. Second-order rate constants for the oxidation of 8-oxo-adenine or 8-oxo-guanine in 1 as a function of base pairing in the complementary strands. The black bars are for 8OG and the gray bars are for 8OA. Rate constants were determined by digital simulation as described previously. Error bars are the standard deviations determined from three independent experiments.

FIG. 11 shows cyclic voltammograms of oligonucleotide 1 with 50 μM $Os(bpy)_3^{2+}$, 50 μM $Fe(bpy)_3^{2+}$ in 50 mM $NaP_i$ buffer with 800 mM NaCl at pH 7. The rate constants for oxidation of 8OG (by $Os(bpy)_3^{3+}$) and 8OA (by $Fe(bpy)_3^{3+}$) are shown in FIG. 12. As shown in the Figure, a large rate constant is observed for each base in the single-strand. When the 8OG is paired to C, the rate constant is lowest. When the 8OG is hybridized to an A, a rate constant in between those of the C and single strand is observed. Similarly, when 8OA is paired with T, the lowest rate constant is observed, while a higher current is observed when 8OA is paired with G. The sensitivity of the rate constants to mismatch does not depend on whether the other preselected base is matched or mismatched.

The foregoing examples are illustrative of the present invention, and are not to be construed as limiting thereof. The invention is described by the following claims, with equivalents of the claims to be included therein.

What is claimed is:

1. A method of detecting two different target molecules through a single common electrode, comprising the steps of:

(a) providing a conductive oxidation-reduction reaction detection electrode;

(b) contacting a sample suspected of containing a first and second target molecule to said detection electrode under conditions in which said first and second target molecules are deposited on said detection electrode, wherein said first target molecule comprises a first preselected label, said second target molecule comprises a second preselected label, and said first and second preselected labels are different;

(c) simultaneously contacting to said electrode (i) a first transition metal complex that oxidizes said first preselected label in an oxidation-reduction reaction to cause a first oxidation-reduction reaction between the first transition metal complex and the first preselected label and (ii) a second transition metal complex that oxidizes said first and second preselected labels in an oxidation-reduction reaction to cause a second oxidation-reduction reaction between the second transition metal complex and the second preselected label, from which preselected labels there is electron transfer to the corresponding transition metal complexes resulting in regeneration of the reduced form of the transition metal complex as part of a catalytic cycle, with said first and second oxidation-reduction reactions producing different detectable signals;

(d) detecting the presence of said first target molecule by detecting said first oxidation-reduction reaction; and (e) detecting the presence of said second target molecule by detecting said second oxidation-reduction reaction.

2. The method according to claim 1, wherein:

said sample is suspected of containing a third target molecule;

said third target molecule comprises a third preselected label that is different from said first and second preselected labels;

said contacting step (c) further comprises contacting to said electrode (iii) a third transition metal complex that oxidizes said first, second and third preselected labels in an oxidation-reduction reaction to cause a third oxidation-reduction reaction between the third transition metal complex and the third preselected label, with said first, second and third oxidation-reduction reactions producing different detectable signals; said method further comprising the step of:

(f) detecting the presence of said third target molecule by detecting said third oxidation-reduction reaction.

3. The method according to claim 2, wherein:

said sample is suspected of containing a fourth target molecule;

said fourth target molecule comprises a fourth preselected label that is different from said first, second and third preselected labels;

said contacting step (c) further comprises contacting to said electrode (iv) a fourth transition metal complex that oxidizes said first, second, third and fourth preselected labels in an oxidation-reduction reaction to cause a fourth oxidation-reduction reaction between the fourth transition metal complex and the fourth preselected label, with said first, second, third and fourth oxidation-reduction reactions producing different detectable signals; said method further comprising the step of:

(g) detecting the presence of said fourth target molecule by detecting said fourth oxidation-reduction reaction.

4. The method according to claim 1, wherein said contacting step (b) is carried out by precipitation.

5. The method according to claim 1, wherein said contacting step (b) is carried out by affinity binding.

6. The method according to claim 1, wherein said transition metal complex is selected from the group consisting of $Ru(bpy)_3^{2+}$, $Ru(Me_2\text{-}bpy)_3^{2+}$, $Ru(Me_2\text{-}phen)_3^{2+}$, $Fe(bpy)_3^{2+}$, $Fe(5\text{-}Cl\text{-}phen)_3^{2+}$, $Os(5\text{-}Cl\text{-}phen)_3^{2+}$, and $ReO_2(py)_4^{1+}$.

7. The method according to claim 1, wherein said first and second preselected labels are selected from the group consisting of adenine, guanine, and analogs thereof.

8. The method according to claim 1, wherein said first and second preselected labels are selected from the group consisting of adenine, 7-deazaadenine, guanine, 6-mercaptoguanine, 8-oxoguanine, isoguanine, 7-deazaguanine, 1hydroxyisoguanine, and 8 bromoguanine.

9. The method according to claim 1, wherein said electrode is carried by a microelectronic substrate.

10. The method according to claim 1, wherein said electrode comprises indium tin oxide.

11. The method according to claim 1, wherein each of said target molecules is a nucleic acid.

12. The method according to claim 11, wherein said contacting step (b) is preceded by the step of amplifying each said nucleic acid.

13. The method according to claim 11, wherein said contacting step (b) is preceded by the step of amplifying each said nucleic acid with an amplification reaction selected from the group consisting of polymerase chain reaction, strand displacement amplification, ligase chain reaction, and nucleic acid sequence-based amplification.

14. The method according to claim 11, wherein said target molecules are selected from the group consisting of DNA and RNA.

15. The method according to claim 1, wherein said target molecules are proteins or peptides.

16. The method according to claim 1, wherein one of said target molecules is a nucleic acid and the other of said target molecules is a protein or peptide.

17. The method according to claim 1, wherein said detecting steps are carried out by multiple step chronoamperometry.

18. The method according to claim 1, wherein said contacting step is carried out by sandwich assay.

19. The method according to claim 1, wherein said contacting steps is carried out by competitive assay.

20. The method according to claim 1, wherein said contacting step is carried out by direct assay.

21. The method according to claim 1, wherein said contacting step is carried out by competitive assay for an immobilized target substance.

22. The method according to claim 1, wherein said contacting step is carried out by binding interaction assay.

* * * * *

UNITED STATES PATENT AND TRADEMARK OFFICE
CERTIFICATE OF CORRECTION

PATENT NO.       : 7,202,028 B2                                              Page 1 of 1
APPLICATION NO.  : 10/237842
DATED            : April 10, 2007
INVENTOR(S)      : Thorp et al.

It is certified that error appears in the above-identified patent and that said Letters Patent is hereby corrected as shown below:

Column 5,
Lines 3 - 11: Please correct paragraph to read: --Figure 2 shows a schematic representation of the strategy used to generate 330 and 1200 base pair PCR products using *E. coli dacA* gene as the template. Primer sequences: CAT GAA TAC CAT TTT TTC CGC TC (up; base pairs 242-264, SEQ ID NO:1), CGG GTT ACC GGT GGC CCA T (mid; base pairs 554-572, SEQ ID NO:2), and TTT AAC CAA ACC AGT GAT GGA ACA TT (down, base pairs 1430-1455, SEQ ID NO:3). Also are shown approximate positions of *Sma*1, *Cla*1, *and Nsp*1 restriction sites.--

Column 26,
Lines 23 - 34: Please correct Table to read as the following:

| Oligonucleotide | DNA Sequence (5' → 3') |
|---|---|
| 1 | AAA TAT A8OAT ATA ATA 8OGAT AAT AAA (SEQ ID NO:4) |
| 2 | TTT ATT ATC TAT TAT ATT ATA ATA TTT (SEQ ID NO:5) |
| 3 | TTT ATT ATA TAT TAT ATT ATA ATA TTT (SEQ ID NO:6) |
| 4 | TTT ATT ATC TAT TAT AGT ATA ATA TTT (SEQ ID NO:7) |
| 5 | TTT ATT ATA TAT TAT AGT ATA ATA TTT (SEQ ID NO:8) |

Signed and Sealed this

Twenty-fifth Day of November, 2008

JON W. DUDAS
*Director of the United States Patent and Trademark Office*

```
                              SEQUENCE LISTING

<160> NUMBER OF SEQ ID NOS: 8

<210> SEQ ID NO 1
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 1
catgaatacc atttttccg ctc                                                23

<210> SEQ ID NO 2
<211> LENGTH: 19
<212> TYPE: DNA
<213> ORGANISM: Artificial sequence
<220> FEATURE:
<223> OTHER INFORMATION: Synthetic oligonucleotide primer

<400> SEQUENCE: 2
cgggttaccg gtggcccat                                                   19

<210> SEQ ID NO 3
<211> LENGTH: 26
<212> TYPE: DNA
<213> ORGANISM: Artificial sequence
<220> FEATURE:
<223> OTHER INFORMATION: Synthetic oligonucleotide primer

<400> SEQUENCE: 3
tttaaccaaa ccagtgatgg aacatt                                           26

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n represents 8-oxoadenine
<220> FEATURE:
<221> NAME/KEY: misc_feature
<222> LOCATION: (16)..(16)
<223> OTHER INFORMATION: n represents 8-oxoguanine

<400> SEQUENCE: 4
aaatatanta taatanataa taaa                                             24

<210> SEQ ID NO 5
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 5
tttattatct attatattat aatatttt                                         27
```

```
<210> SEQ ID NO 6
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 6
tttattatat attatattat aatattt                                27

<210> SEQ ID NO 7
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 7
tttattatct attatagtat aatattt                                27

<210> SEQ ID NO 8
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 8
tttattatat attatagtat aatattt                                27
```